(12) United States Patent
Song et al.

(10) Patent No.: US 8,735,071 B2
(45) Date of Patent: May 27, 2014

(54) COMPOSITIONS FOR PROMOTING EPIGENETIC DNA DEMETHYLATION AND METHODS OF USE THEREFORE

(75) Inventors: Hongjun Song, Clarksville, MD (US); Dengke K. Ma, Cambridge, MA (US); Guo-li Ming, Clarksville, MD (US)

(73) Assignee: The Johns Hopkins University, Baltimore, MD (US)

( * ) Notice: Subject to any disclaimer, the term of this patent is extended or adjusted under 35 U.S.C. 154(b) by 121 days.

(21) Appl. No.: 13/142,134

(22) PCT Filed: Dec. 23, 2009

(86) PCT No.: PCT/US2009/006698
§ 371 (c)(1),
(2), (4) Date: Dec. 14, 2011

(87) PCT Pub. No.: WO2010/074758
PCT Pub. Date: Jul. 1, 2010

(65) Prior Publication Data
US 2012/0088812 A1    Apr. 12, 2012

Related U.S. Application Data

(60) Provisional application No. 61/140,702, filed on Dec. 24, 2008.

(51) Int. Cl.
| | |
|---|---|
| *G01N 33/15* | (2006.01) |
| *G01N 33/68* | (2006.01) |
| *G01N 33/53* | (2006.01) |
| *C12Q 1/68* | (2006.01) |
| *A61K 31/7088* | (2006.01) |

(52) U.S. Cl.
USPC ....... 435/6.13; 514/44 R; 435/6.16; 435/7.21; 435/39; 435/375

(58) Field of Classification Search
None
See application file for complete search history.

(56) References Cited

PUBLICATIONS

Kojima et al. FEBS Letters 446 (1999) 313-317.*
Tonchev et al., Differential Proliferative Response in the Postischemic Hippocampus, Temporal Cortex, and Olfactory Bulb of Young Adult Macaque Monkeys. GLIA 42:209-224 (2003).*
Liebermann et al., Gadd45 in stress signaling. Journal of Molecular Signaling 2008, 3:15, 1-8.*
Barreto et al., "Gadd45a promotes epigenetic gene activation by repair-mediated DNA demethylation", Nature, vol. 445, pp. 671-675 (2007).
Zhang et al., "Loss of Expression of GADD45γ, a Growth Inhibitory Gene, in Human Pituitary Adenomas: Implications for Tumorigenesis", The Journal of Clinical Endocrinology & Metabolism, vol. 87(3), pp. 1262-1267 (2002).
Hildesheim et al., "Gadd45a: An Elusive Yet Attractive Candidate Gene in Pancreatic Cancer", Clinical Cancer Research, vol. 8(8), pp. 2475-2479 (2002).
Jin et al., "GADD45A Does Not Promote DNA Demethylation", PLOS Genetics, vol. 4(3), pp. 1-9 (2008).
Lal et al., "Egad, More Forms of Gene Regulation: The gadd45a Story", Cell Cycle, vol. 5(13), pp. 1422-1425 (2006).
Ma et al., "Neuronal Activity-Induced Gadd45b Promotes Epigenetic DNA Demethylation and Adult Neurogenesis", Science, vol. 323(5917), pp. 1074-1077 (2009).

* cited by examiner

*Primary Examiner* — Jeffrey Stucker
*Assistant Examiner* — Aurora M Fontainhas
(74) *Attorney, Agent, or Firm* — John Hopkins Technology Transfer

(57) ABSTRACT

The invention features compositions and methods for modulating the expression of Gadd45 and the use of such compositions and methods as neuroprotectants, to enhance neurogenesis, and for the treatment of mood disorders.

1 Claim, 23 Drawing Sheets

COMPOSITIONS FOR PROMOTING EPIGENETIC DNA DEMETHYLATION AND METHODS OF USE THEREFORE

CROSS-REFERENCE TO RELATED APPLICATIONS

This application is a 35 U.S.C. §371 U.S. national entry of International Application PCT/US2009/006698 (WO 2010/074758) having an International filing date of Dec. 23, 2009 which claims the benefit of the following U.S. Provisional Application No. 61/140,702, filed Dec. 24, 2008, the entire contents of which are incorporated herein by reference.

STATEMENT OF RIGHTS TO INVENTIONS MADE UNDER FEDERALLY SPONSORED RESEARCH

This work was supported by the following grants from the National Institutes of Health, Grant Nos: NS047344 and AG024984. The government has certain rights in the invention.

BACKGROUND OF THE INVENTION

Adult neurogenesis represents a striking form of structural plasticity in the mature mammalian brain. One hallmark of adult neurogenesis is its modulation by a plethora of external stimuli in an activity-dependent manner. For example, electroconvulsive treatment (ECT) of adult mice induces highly synchronized activation of mature dentate neurons without detectable excitotoxicity and causes sustained up-regulation of hippocampal neurogenesis and a lasting treatment for depression. How transient activation of existing neuronal circuits leads to such long lasting effects is largely unknown. Epigenetic mechanisms provide a basis for long-lasting modulation of neurogenesis, as well as mediating activity-dependent regulation of neural plasticity. Compositions and methods capable of modulating activity-dependent neural plasticity would likely be useful as neuroprotectants and for the treatment of mood disorders.

SUMMARY OF THE INVENTION

As described below, the present invention features compositions and methods for modulating the expression of Gadd45, which links neuronal activity to DNA demethylation, and the use of such compositions and methods as neuroprotectants, to enhance neurogenesis, and for the treatment of mood disorders.

In one aspect, the invention provides a method for identifying an agent that modulates expression of a Gadd45 polynucleotide in a neuronal cell, the method involving contacting a neuronal cell containing a Gadd45 polynucleotide with an agent; and comparing the level of Gadd45 polynucleotide expression in the presence of the agent with the level of Gadd45 expression in the absence of the agent; where a measurable difference in Gadd45 expression indicates that the agent modulates gene expression of a Gadd45 polynucleotide. In one embodiment, the method identifies an agent that increases or decreases (e.g., by at least about 10%, 25%, 50%, 75% or more) transcription of the Gadd45 polynucleotide. In another embodiment, the method identifies an agent that increases or decreases (e.g., by at least about 10%, 25%, 50%, 75% or more) translation of an mRNA transcribed from the Gadd45 polynucleotide. In another embodiment, the agent is a polypeptide, polynucleotide, or small compound. In yet another embodiment, Gadd45 polynucleotide expression is assayed by Northern blot, PCR, or a hybridization method.

In another aspect, the invention provides a method for identifying an agent that modulates expression of a Gadd45 polypeptide in a neuronal cell, the method involving contacting a neuronal cell containing a Gadd45 polypeptide with an agent; and comparing the level of Gadd45 polypeptide expression in the presence of the agent with the level of Gadd45 expression in the absence of the agent; where a measurable difference in Gadd45 expression indicates that the agent modulates expression of a Gadd45 polypeptide in a neuronal cell. In one embodiment, Gadd45 polypeptide expression is assayed in an immunoassay, radioassay, ELISA, or Western blot.

In another aspect, the invention provides a method for identifying an agent that modulates DNA demethylation by a Gadd45 polypeptide, the method involving contacting a neuronal cell expressing a Gadd45 polypeptide with an agent; and comparing the DNA demethylation activity of the Gadd45 polypeptide in the presence of the agent with the activity in the absence of the agent; where a measurable difference in the activity indicates that the agent modulates activity of the polypeptide. In one embodiment, the method identifies an agent that increases or decreases Gadd45 DNA demethylation activity. In another embodiment, Gadd45 DNA demethylation activity is region-specific DNA demethylation activity. In another embodiment, the method identifies a reduction in the frequency of methylation. In yet another embodiment, demethylation is assayed in a regulatory region of a polypeptide that functions in neurogenesis. In yet another embodiment, the polypeptide is a growth factor. In another embodiment, Gadd45 demethylation activity is assayed using a methylation-sensitive restriction enzyme, by direct immunostaining of 5-methylcytosine, by chromatin immunoprecipitation (ChIP), or by methylated DNA immunoprecipitation (MeDIP).

In another aspect, the invention provides a method for identifying an agent that enhances neural plasticity, the method involving contacting a neuronal cell containing a Gadd45 polypeptide with an agent; and comparing dendritic complexity or synapse formation in the presence of the agent with dendritic complexity or synapse in the absence of the agent; where an increase in dendritic complexity or synapse formation indicates that the agent enhances neural plasticity. In one embodiment, neuronal plasticity is assayed by measuring dendritic complexity, dendritic length, or synapse formation.

In another aspect, the invention provides a method for identifying an agent that enhances neurogenesis, the method involving contacting a neuronal cell containing a Gadd45 polypeptide with an agent; and comparing neurogenesis in the presence of the agent with neurogenesis in the absence of the agent; where an increase in neurogenesis indicates that the agent enhances neurogenesis. In one embodiment, neural progenitor proliferation is assayed using bromodeoxyuridine. In another embodiment, the method increases neural progenitor cell proliferation.

In another aspect, the invention provides a method for identifying an agent that promotes neuronal survival, the method involving contacting a neuronal cell containing a Gadd45 polypeptide with an agent; inducing cell death in the neuronal cell; and comparing neuronal cell death in the presence of the agent with neuronal cell death in the absence of the agent; where a decrease in neuronal cell death indicates that the agent promotes neuronal survival. In one embodiment, the agent reduces cell death. In another embodiment, cell death is induced by ischemic injury. In another embodiment, the neuron is in vivo or in vitro. In another embodiment, the neuron is a human neuron in vitro or a rodent neuron in vivo. In yet another embodiment, the activity of the agent is dependent upon the presence of a Gadd45 polypeptide or a functional equivalent thereof.

In another aspect, the invention provides a method for reducing Gadd45 polypeptide or polynucleotide expression in a neuronal cell, the method involving contacting the neuronal cell with an inhibitory nucleic acid molecule (e.g., an antisense polynucleotide, siRNA, or shRNA) at least a portion of which specifically binds to a Gadd45 polynucleotide. In one embodiment, the inhibitory nucleic acid molecule is an siRNA that reduces Gadd45 polynucleotide or polypeptide level by at least about 25-50% or more.

In another aspect, the invention provides a method of enhancing neurogenesis in a mammal, the method involving administering to the mammal a therapeutically-effective amount of an agent that induces the expression of or activity of or represses the expression of or activity of a Gadd45 polypeptide.

In another aspect, the invention provides a method of promoting neuronal survival in a mammal, the method involving administering to the mammal a therapeutically-effective amount of an agent that modulates the expression or activity of a Gadd45 polypeptide or polynucleotide. In one embodiment, the mammal has sustained an ischemic injury (e.g., stroke).

In another aspect, the invention provides a method of treating a mood disorder (e.g., depression), the method involving administering to the mammal a therapeutically-effective amount of an agent that modulates the expression or activity of a Gadd45 polypeptide or polynucleotide. In one embodiment, the agent is a polynucleotide encoding a Gadd45 polypeptide. In another embodiment, the agent is an expression vector containing a promoter suitable for expression of Gadd45 in a mammalian neuron.

In another aspect, the invention provides a method for treating a condition characterized by neuronal Gadd45 dysregulation, the method involving contacting a Gadd45 expressing neuron with an agent that modulates Gadd45 expression or biological activity, thereby treating the condition. In one embodiment, the condition is associated with increased levels of Gadd45 expression or biological activity. In another embodiment, the condition is autism or mental retardation. In yet another embodiment, the condition is associated with reduced levels of Gadd45 expression or biological activity. In still another embodiment, the agent is an inhibitory nucleic acid molecule that reduces Gadd45 expression. In another embodiment, the agent is a mammalian expression vector encoding Gadd45. In another embodiment, the expression vector comprises a promoter suitable for expressing Gadd45 in a neuron.

In various embodiments of any of the above aspects or any other aspect of the invention delineated herein, the Gadd45 polypeptide is a polypeptide or fragment thereof having at least about 85%, 90%, 95% or greater identity to Gadd45b and having DNA methylation activity. In other embodiments, the agent targets the Gadd45 polypeptide or a functional equivalent thereof. In still other embodiments, the Gadd45 polypeptide is Gadd45a, Gadd45b, or Gadd45g. In still other embodiments of the above aspects, neuronal plasticity is assayed by measuring dendritic complexity, dendritic length, or synapse formation. In still other embodiments of the above aspects, Gadd45 demethylation activity is assayed using a methylation-sensitive restriction enzyme, by direct immunostaining of 5-methylcytosine, by chromatin immunoprecipitation (ChIP), or by methylated DNA immunoprecipitation (MeDIP).

The invention provides compositions that modulate Gadd45 expression and activity. Compositions and articles defined by the invention were isolated or otherwise manufactured in connection with the examples provided below. Other features and advantages of the invention will be apparent from the detailed description, and from the claims.

Definitions

By "Gadd45 polypeptide" is meant a polypeptide or fragment thereof having at least about 85% amino acid sequence identity to a Gadd45b protein and having DNA demethylation activity. Gadd45 polypeptides include but are not limited to Gadd45 family members, such as Gadd45a, b, and g. In the art the terms Gadd45a, b, and g are used interchangeably with Gadd45a, B, and γ, respectively. An exemplary Gadd45 amino acid sequence is provided at NCBI Accession No. NP_56490:

```
  1 mtleelvacd naaqkmqtvt aaveellvaa qrqdrltvgv yesaklmnvd
    pdsvvlclla
 61 ideeeddia lqihftliqs fccdndiniv rvsgmqrlaq llgepaetqg
    tteardlhcl
121 lvtnphtdaw kshglvevas yceesrgnnq wvpyislqer
```

By "Gadd45 nucleic acid molecule" is meant a polynucleotide encoding a Gadd45 polypeptide or fragment thereof.

By "Gadd45 biological activity" is meant DNA demethylation activity. In one embodiment, Gadd45 biological activity is region specific DNA demethylation activity.

By "condition characterized by neuronal Gadd45 dysregulation" is meant any disease or disorder associated with an increase or decrease in Gadd45 expression or activity in a cell or tissue relative to the expression or activity of Gadd45 in a corresponding control cell or tissue. In one embodiment, Gadd45 expression or activity in a subject having a condition is compared with Gadd45 expression or activity in a healthy control subject.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "modulate" is meant to alter (e.g., increase or decrease) a parameter. An "alteration" is a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases include mood disorders, such as depression, and ischemic injury, particularly neuronal cell death caused by brain injury, spinal cord injury, stroke or other ischemic injury.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The invention provides a number of targets, such as GADD45 polypeptides, that are useful for the development of highly specific drugs to treat or a disorder characterized by the methods delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "inhibitory nucleic acid" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein. In one embodiment, the invention provides an inhibitory nucleic acid molecule (e.g., shRNA) that reduces Gadd45 polypeptide expression.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

As used herein, "obtaining" as in "obtaining an agent" includes synthesizing, purchasing, or otherwise acquiring the agent.

By "increases" is meant a positive alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 .mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A is a Western blot. Dentate gyrus tissue from adult Gadd45 WT and KO mice without ECT or at 1 or 4 hrs after a single ECT was subjected to Western blot analysis (A) of Caspase3-a (activated form of caspase3) expression or ATM phosphorylation (at the amino acid residue 1981). Lysate from primary hippocampal cultures treated with 1 µM Staurosporine was used as a positive control for comparison. Actin was used as the loading control. FIG. 1B provides confocal images of dentate gyrus before or at 1 hr after ECT for immunostaining of ATM-p1981 and DAPI. Note that very few cells were positive for ATM-p1981 (arrows). Scale bar: 20 µm.

FIG. 2A is a graph showing the results of a Q-PCR analysis of ECT-induced expression of Gadd45a, Gadd45b and Gadd45g in the adult dentate gyrus after a single ECT. FIG. 2B provides six sample images of Gadd45b in situ hybridization of the adult hippocampus after ECT. Scale bar: 0.5 mm. FIG. 2C is a graph that quantitates Gadd45 induction in the dentate gyrus after 1 hr spatial exploration of novel environment. FIG. 2C provides a summary from Q-PCR analysis. Shown in FIG. 2D are sample confocal images of Gadd45b in situ hybridization, DAPI and Arc immunostaining. Note that the majority of Gadd45b-positive cells (open and closed arrowheads) were Arc-positive (closed arrowheads). Scale bar: 50 µm. FIG. 2E provides three graphs that quantitate NMDAR-dependent induction of Gadd45b, Arc and Homer1 in the adult dentate gyrus at 1 hr after ECT. The NMDAR antagonist 3-(2-carboxypiperzin-4-yl)-propyl-1-phosphonoc acid (CPP) was injected at 1 hr before ECT (10 mg/kg body weight, i.p.). Values represent mean±SEM (n=4; *: P<0.01, ANOVA).

FIG. 5A is a graph that summarizes the time course of Gadd45b expression after $K^+$ stimulation (50 mM) by Q-PCR analysis. FIG. 5B is a graph that summarizes $K^+$-induced Gadd45b expression without (control) or with specific pharmacological manipulations by Q-PCR analysis. Cultures were pretreated with BAPTA (50 µM), Nimodipin (10 µM), KN92 or KN93 (10 µM) for 0.5 hr and then stimulated with $K^+$ for 1 hr. FIG. 5C is a graph that summarizes Gadd45b expression with manipulation of neurotransmitter signaling by Q-PCR analysis. Neurons were stimulated with saline, glutamate (20 µM), APV (0.2 mM) pre-treatment and glutamate (20 µM), APV (0.2 mM), bicuculline (50 µM), or APV (0.2 mM) pre-treatment and bicuculline (50 µM), respectively. Gadd45b expression was analyzed with Q-PCR. Values were normalized to those of β-actin for each sample and then normalized to the control group. Values represent mean±SEM (n=5; *: P <0.05, ANOVA).

FIG. 7A shows sample projected confocal images of BrdU immunostaining (red) and DAPI (Blue). Scale bar: 50 µm. FIG. 7B is a graph that summarizes stereological quantification of $BrdU^+$ cells in the dentate gyrus. Values represent mean±SEM (n=4-5 animals as indicated; *: P<0.01, ANOVA).

FIG. 8A shows a sample confocal image of activated caspase-3 immunostaining (red, arrow) and DAPI nucleus staining (blue). Scale bar: 50 µm. FIG. 8B is a graph that summarizes the quantification of the density of activated caspase-3 positive cells within the subgranular layer and granule cell layer, or at 3 days after ECT. For comparison, the density of BrdU labeled cells in WT adult animals is also shown. Values represents mean±SEM (n=3-5).

FIGS. 9A-9C provide confirmation of the effectiveness of shRNA against Gadd45b in vitro and in vivo. Shown in (A) is Western blot analysis of HEK293T lysates after co-transfection of shRNA and expression construct for Gadd45b-GFP. FIG. 9B is a graph that summarizes the results of Q-PCR analysis of endogenous Gadd45b expression in primary hippocampal neurons after infection with lentiviruses expressing shRNAs. Values represent mean±SEM (n=3; P<0.01, ANOVA). In FIG. 9C shows that high titers of lentiviruses co-expressing GFP and specific shRNA against Gadd45b or control shRNA were stereotaxically injected into the dentate gyrus of the adult WT mice. At 7 days after viral injection, animals were subjected to a single ECT and the whole brain was freshly frozen 1 hr later using 2-methylbutane and processed with cryostat. Tissues containing GFP$^+$ cells from the dentate gyrus sections were immediately collected for expression analysis. FIG. 9C (bottom panel) is a graph summary of expression of the endogenous Gadd45b or Gadd45g by Q-PCR. Values represent mean±SEM (n=3; *: P<0.01, ANOVA). FIG. 9D is a schematic diagram of the experimental design for analysis of cell proliferation. FIG. 9E shows sample confocal projection images of BrdU immunostaining (red), DAPI (blue) and GFP (green). Scale bar: 50 µm. FIG. 9F is a graph that summarizes stereological quantification of BrdU$^+$ cells in the GFP$^+$ regions of the dentate gyrus. Values represent mean±SEM (n=4-7 animals as indicated; *: P<0.01, ANOVA).

FIG. 10B shows the effect of running on the proliferation of neural progenitors in the dentate gyrus of adult Gadd45b WT and KO mice. Littermates of adult Gadd45b WT and KO mice were housed with or without free access to running wheels for 7 days before BrdU (200 mg/kg body weight, i.p.) injection and animals were perfused 2 hrs later for analysis. Shown is a summary of stereological quantification of BrdU$^+$ cells in the dentate gyrus. Values represent mean±SEM (n=4 animals; *: P<0.01, ANOVA).

FIG. 11A shows a sample projected Z-series confocal images of GFP$^+$ dentate granule cells at 14 days after viral labelling. Scale bar: 50 µm. FIG. 11B is a graph that quantifies the total dendritic length of GFP$^+$ dentate granule cells. Values represent mean±SEM (n=23-45 neurons for each condition; *: P<0.01, ANOVA). FIG. 11C is a graph that shows an analysis of dendritic complexity of the same group of cells as in (FIG. 11B; *: P <0.01, Student t-test).

FIG. 12A shows results of an analysis of global DNA demethylation with methylation sensitive enzyme McrBC. Linearized control methylated plasmids containing one McrBC site and genomic DNA from dentate gyrus at 4 hrs after ECT or sham controls were treated with McrBC and analyzed by electrophoresis. FIG. 12B shows an analysis of global DNA methylation with immunocytochemistry. Adult mice received sham treatment or at 4 hrs after ECT were processed for immunostaining with antibodies against 5-methylcytosine and nucleus staining with DAPI. Shown are sample confocal images. Scale bar: 25 µm.

FIG. 13A is a schematic diagram for analysis of DNA methylation and gene expression in the adult dentate gyrus. FIG. 13B shows that ECT-induced changes in the methylation level at regulatory regions of selective genes. Genomic DNA was isolated from micro-dissected dentate gyrus tissue, digested with MseI and immunoprecipitated with 5-methylcytosine specific antibodies. The enrichment of DNA methylation relative to input genomic DNA at specific regions was quantified by Q-PCR using specific primers (listed in Table 1). Shown on the left are sample images and on the right is the summary of quantification of DNA methylation levels of different genomic regions. Values represent mean±SEM (n=3; *: P<0.05, ANOVA). FIG. 13C is a graph showing the role of Gadd45b in ECT-induced DNA demethylation in the dentate gyrus of the adult brain. The results provided here are similar to those provided at FIG. 13B, except that both Gadd45b WT and KO mice with sham treatment or at 4 hrs after ECT were examined. Values represent mean±SEM (n=3; *: P<0.05, ANOVA).

FIG. 14A-B show results of a bisulfite sequencing analysis of adult dentate gyms tissue before or at 4 hrs after ECT. Shown in FIG. 14A is a schematic diagram of the genomic region subjected to analysis and a summary of methylation frequency at individual CpG sites. Shown in FIG. 14B is a summary of mean DNA methylation levels of individual alleles. Values represent mean±SEM (n=10-15; **: P<0.01; *: P<0.05; #: P>0.1, ANOVA; See exact P values in Table 2). FIG. 14C shows results of a methylation-specific PCR analysis from the dentate gyrus of WT mice after one or two ECTs ("24+4": 4 hrs after two ECTs at 24 hrs apart), or 7 days after lentivirus-mediated expression of Gadd45b-GFP or GFP alone without ECT. Primers are specific for methylated (M) and un-methylated alleles (UM) of the FGF-1B promoter, or for bisulfite sequencing without CpGs (Input).

FIG. 15A is a schematic diagram showing that Gadd45b functions in ECT-induced DNA demethylation of BDNF IX and FGF-1B regulatory regions in the adult dentate gyrus. Shown on the top is a schematic diagram of the genomic region subjected to analysis. Scale bar: 100 bp. Shown below is a display of bisulfite sequencing reads of individual alleles for each gene. Filled (black) or open (yellow) boxes represent methylated or unmethylated CpG sites, respectively. Numbers indicate the mean frequency of methylation at all CpG sites examined. FIG. 15A (top panel) is a schematic diagram showing no change in DNA methylation status in the regulatory regions of FGF-1G and Oct4 in the adult dentate gyrus after ECT.

FIG. 15A is a schematic diagram of the genomic region subjected to bisulfite sequencing analysis relative to the transcriptional start site is shown with individual CpG site color-coded. Shown in FIG. 15A is a display of bisulfite sequencing reads of individual allele. Filled (black) or open (yellow) boxes represent methylated and unmethylated CpG sites, respectively. Shown in the top panel are reads of those at different time points after a single ECT to examine the dynamics of DNA demethylation and re-methylation. Shown in the lower panel are reads from those received a second ECT at 24 hrs after the first ECT to examine re-activation. Numbers indicate the mean frequency of methylation at all CpG sites examined. FIG. 15B includes two graphs. Shown in FIG. 15B is a summary of frequency of methylation at individual CpG sites (1-8) at different time points after the first or second ECT. Note the rapid and robust demethylation at all CpG sites examined at 4 hrs after ECT and gradual re-methylation of these sites within 16-24 hrs to a level still slightly lower than those before ECT for the majority of sites (except Site 5). Also note the robust demethylation after the second ECT and re-methylation afterwards.

FIG. 17A is a schematic diagram of the genomic region subjected to bisulfite sequencing analysis relative to the transcriptional start site is shown with individual CpG site color-coded (1-7). Shown in FIG. 17A is a display of bisulfite sequencing reads of individual allele. Filled (black) or open (yellow) boxes represent methylated and unmethylated CpG sites, respectively. Shown in the top panel are reads of those at different time points after a single ECT to examine the dynamics of DNA demethylation and re-methylation. Shown in the lower panel are reads from those received a second ECT at 24 hrs after the first ECT to examine re-activation. Numbers indicate the mean frequency of methylation at all CpG sites examined. FIG. 17B includes two graphs that summarize the frequency of methylation at individual CpG sites (1-7) at different time points after the first or second ECT. Note the rapid and robust demethylation at all CpG sites examined at 4 hrs after ECT and gradual re-methylation of these sites within 16-24 hrs to a level still slightly lower than those before ECT for several sites. Also note the robust demethylation after the second ECT and re-methylation afterwards.

FIG. 19C includes sample images of GFP, tdTomato and immunostaining of a neuronal marker MAP2ab. Scale bar: 50 µm. FIG. 19D is a graph that summarizes the percentage of GFP$^+$ neurons among all tdTomato$^+$ neurons under different conditions. Values represent mean±SEM (n=8; *: P<0.05, ANOVA).

FIG. 23A shows micrographs of adherent cultures of adult multi-potent, self-renewing rat neural progenitors was plated on laminin and polyornithine-coated dishes in the presence of various concentrations of FGF-1 (0, 2, 5, 10 and 20 ng/ml) or the known mitogen FGF-2 (20 ng/ml). FIG. 23B is a graph showing cell number as a function of FGF concentration. At 4 days in vitro, cell numbers from each condition were determined by counting from randomly selected fields of 4 different biological replicates. Values represent mean±SEM (n=4; *: P<0.05, ANOVA).

DETAILED DESCRIPTION OF THE INVENTION

Figure 1:
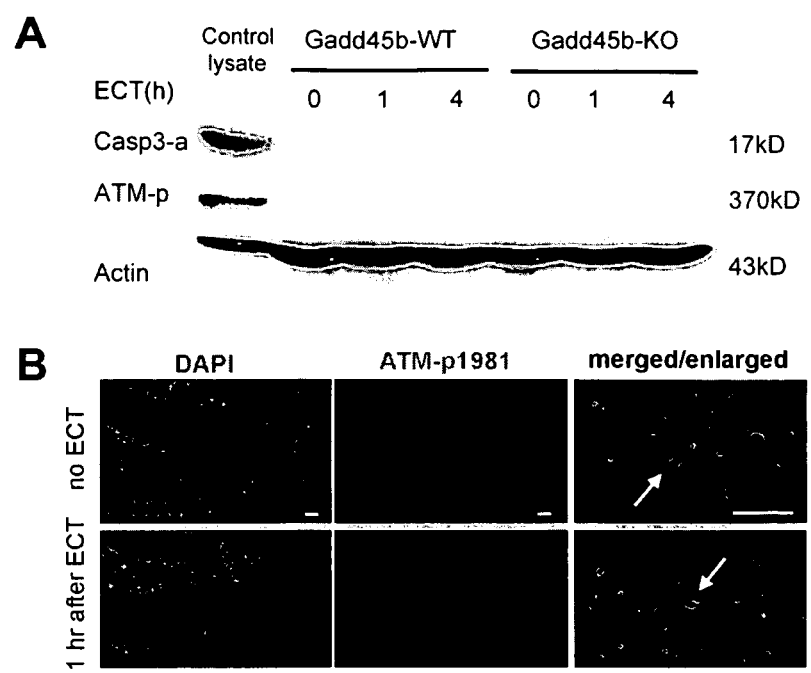
FIGS. 1A and 1B show lack of significant cell death and excitotoxicity after ECT in the dentate gyrus of adult mouse hippocampus.

The invention features compositions and methods that modulate Gadd45 expression or activity (e.g., DNA demethylation activity). Agents that modulate Gadd45 region specific DNA demethylation activity are useful in enhancing neural plasticity, promoting neurogenesis, as neuroprotectants (e.g., by promoting neuronal survival or reducing cell death), or to treat a mood disorder, such as depression.

The invention is based, at least in part, on the discovery of that Gadd45b is a neural activity-induced immediate early gene in mature hippocampal neurons. Mice with Gadd45b deletion had specific deficits in neural activity-induced proliferation of neural progenitors and dendritic growth of newborn neurons in the adult hippocampus. Mechanistically, Gadd45b is required for activity-induced DNA demethylation of specific promoters and expression of corresponding genes critical for adult neurogenesis, including BDNF and FGF. Thus, Gadd45b links neuronal circuit activity to epigenetic DNA modification and expression of secreted factors in mature neurons for extrinsic modulation of neurogenesis in the adult brain.

Gadd45 Polypeptide Expression

In general, Gadd45 polypeptides of the invention (e.g., Gadd45a, b, g) may be produced by transformation of a suitable host cell with all or part of a Gadd45 nucleic acid molecule or fragment thereof in a suitable expression vehicle. Such recombinant polypeptides may be used in screening methods described herein.

Those skilled in the field of molecular biology will understand that any of a wide variety of expression systems may be used to provide the recombinant protein. The precise host cell used is not critical to the invention. A polypeptide of the invention may be produced in a prokaryotic host (e.g., *E. coli*) or in a eukaryotic host (e.g., *Saccharomyces cerevisiae*, insect cells, e.g., Sf21 cells, or mammalian cells, e.g., NIH 3T3, HeLa, or preferably COS cells). Such cells are available from a wide range of sources (e.g., the American Type Culture Collection, Rockland, Md.; also, see, e.g., Ausubel et al., supra). The method of transformation or transfection and the choice of expression vehicle will depend on the host system selected. Transformation and transfection methods are described, e.g., in Ausubel et al. (supra); expression vehicles may be chosen from those provided, e.g., in Cloning Vectors: A Laboratory Manual (P. H. Pouwels et al., 1985, Supp. 1987).

One particular bacterial expression system for polypeptide production is the *E. coli* pET expression system (Novagen, Inc., Madison, Wis.). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7 RNA polymerase in the host cell. This is typically achieved using host strains which express T7 RNA polymerase in response to IPTG induction. Once produced, recombinant polypeptide is then isolated according to standard methods known in the art, for example, those described herein.

Another bacterial expression system for polypeptide production is the pGEX expression system (Pharmacia). This system employs a GST gene fusion system which is designed for high-level expression of genes or gene fragments as fusion proteins with rapid purification and recovery of functional gene products. The protein of interest is fused to the carboxyl terminus of the glutathione S-transferase protein from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3X may be cleaved with factor Xa.

Once the recombinant polypeptide of the invention is expressed, it is isolated, e.g., using affinity chromatography. In one example, an antibody (e.g., produced as described herein) raised against a polypeptide of the invention may be attached to a column and used to isolate the recombinant polypeptide. Lysis and fractionation of polypeptide-harboring cells prior to affinity chromatography may be performed by standard methods (see, e.g., Ausubel et al., supra).

Once isolated, the recombinant protein can, if desired, be further purified, e.g., by high performance liquid chromatography (see, e.g., Fisher, Laboratory Techniques In Biochemistry And Molecular Biology, eds., Work and Burdon, Elsevier, 1980).

Polypeptides of the invention, particularly short peptide fragments, can also be produced by chemical synthesis (e.g., by the methods described in Solid Phase Peptide Synthesis, 2nd ed., 1984 The Pierce Chemical Co., Rockford, Ill.). Also included in the invention are polypeptides which are modified in ways which do not abolish their region-specific DNA demethylation activity (assayed, for example as described herein). Such changes may include certain mutations, deletions, insertions, or post-translational modifications, or may involve the inclusion of any of the polypeptides of the invention as one component of a larger fusion protein.

The invention further includes analogs of any naturally-occurring polypeptide of the invention. Analogs can differ from the naturally-occurring the polypeptide of the invention by amino acid sequence differences, by post-translational modifications, or by both. Analogs of the invention will generally exhibit at least 85%, more preferably 90%, and most preferably 95% or even 99% identity with all or part of a naturally-occurring amino acid sequence of the invention. The length of sequence comparison is at least 15 amino acid residues, preferably at least 25 amino acid residues, and more preferably more than 35 amino acid residues. Again, in an exemplary approach to determining the degree of identity, a BLAST program may be used, with a probability score between $e^{-3}$ and $e^{-100}$ indicating a closely related sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the invention by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., .beta. or .gamma. amino acids.

In addition to full-length polypeptides, the invention also includes fragments of any one of the polypeptides of the invention. As used herein, the term "fragment," means at least 5, preferably at least 20 contiguous amino acids, preferably at least 30 contiguous amino acids, more preferably at least 50 contiguous amino acids, and most preferably at least 60 to 80 or more contiguous amino acids. Fragments of the invention can be generated by methods known to those skilled in the art or may result from normal protein processing (e.g., removal of amino acids from the nascent polypeptide that are not required for biological activity or removal of amino acids by alternative mRNA splicing or alternative protein processing events). The aforementioned general techniques of polypeptide expression and purification can also be used to produce and isolate useful peptide fragments or analogs (described herein).

Gadd45 Assays

As discussed above, the present invention identifies Gadd45 as regulating region-specific DNA demethylation. Based on this discovery, assays are provided for identifying agents that enhance or inhibit the biological activity of a Gadd45 polypeptide or the expression of a Gadd45 nucleic acid sequence of the invention. Agents identified using such methods are useful in treating a disease or disorder characterized by a dysregulation in Gadd45 expression or activity, or a condition where an increase or decrease in Gadd45 expression or activity is desired. The methods of the invention may involve high-throughput techniques. In one embodiment, an agent which promotes an increase in the expression of the Gadd45 gene or a functional equivalent is considered useful in the invention; such a molecule may be used, for example, as a therapeutic to modulate region-specific DNA demethylation, enhance neural plasticity, enhance neurogenesis, as a neuroprotectant (e.g., to promote neuronal survival), or to treat a mood disorder, such as depression.

Any number of methods are available for carrying out such assays. In one example, candidate agents are added at varying concentrations to the culture medium of cells expressing one of the nucleic acid sequences of the invention. Gene expression is then measured, for example, by standard Northern blot analysis (Ausubel et al., supra) or RT-PCR, using any appropriate fragment prepared from the nucleic acid molecule as a hybridization probe. The level of gene expression in the presence of the candidate agent is compared to the level measured in a control culture medium lacking the candidate molecule.

In another example, the effect of candidate agents is measured at the level of polypeptide production using the same general approach and standard immunological techniques, such as Western blotting or immunoprecipitation with an antibody specific for a Gadd45 polypeptide, such as Gadd45b. For example, immunoassays may be used to detect or monitor the expression of at least one of the polypeptides of the invention in an organism. Polyclonal or monoclonal antibodies (produced as described above) which are capable of binding to such a polypeptide may be used in any standard immunoassay format (e.g., ELISA, Western blot, or RIA assay) to measure the level of the polypeptide. An agent which promotes an increase in the expression of the polypeptide is considered particularly useful. Again, such a molecule may be used, for example, as a therapeutic to modulate region-specific DNA demethylation, enhance neural plasticity, enhance neurogenesis, as a neuroprotectant (e.g., to promote neuronal survival), or to treat a mood disorder, such as depression as described herein.

In yet another example, candidate agents are screened for those which specifically bind to and modulate the activity of a Gadd45 polypeptide of the invention. The efficacy of such a candidate agent is dependent upon its ability to interact with the Gadd45 polypeptide or functional equivalent thereof. Such an interaction can be readily assayed using any number of standard binding techniques and functional assays (e.g., those described in Ausubel et al., supra). For example, a candidate agent may be tested in vitro for interaction and binding with a Gadd45 polypeptide of the invention and its ability to modulate region-specific DNA demethylation, neurogenesis, neuroprotective activity, or neuronal plasticity, may be assayed by any standard assay (e.g., those described herein).

In one particular example, a candidate agent that binds to a polypeptide (e.g, Gadd45) may be identified using a chromatography-based technique. For example, a recombinant Gadd45 polypeptide of the invention may be purified by standard techniques from cells engineered to express the polypeptide (e.g., those described above) and may be immobilized on a column. A solution of candidate agents is then passed through the column, and an agent specific for the Gadd45 polypeptide is identified on the basis of its ability to bind to the Gadd45 polypeptide and be immobilized on the column. To isolate the agent, the column is washed to remove non-specifically bound molecules, and the agent of interest is then released from the column and collected. Agents isolated by this method (or any other appropriate method) may, if desired, be further purified (e.g., by high performance liquid chromatography). In addition, these candidate agents may be tested for their ability to modulate region-specific DNA demethylation, neurogenesis, neuroprotective activity, or neuronal plasticity, may be assayed by any standard assay (e.g., those described herein) (e.g., as described herein). Agents isolated by this approach may also be used, for example, as therapeutics to treat or prevent neuronal cell death, as a neuroprotectant to promote neuronal survival (e.g., neuronal survival after stroke or another ischemic event) or to treat a mood disorder, such as depression. Agents which are identified as binding to a Gadd45 polypeptides (e.g, Gadd45b) with an affinity constant less than or equal to 10 mM are considered particularly useful in the invention.

Potential Gadd45 modulators include organic molecules, peptides, peptide mimetics, polypeptides, and antibodies that bind to a Gadd45 nucleic acid sequence or Gadd45 polypeptide of the invention (e.g, Gadd45b) and thereby increase its activity.

Each of the DNA sequences provided herein may also be used in the discovery and development of agents that promote neuronal survival or treat a mood disorder, such as depression. The encoded protein, upon expression, can be used as a target for the development of neuroprotective or neuroactive agents. Additionally, the DNA sequences encoding the amino terminal regions of the encoded protein or Shine-Delgarno or other translation facilitating sequences of the respective mRNA can be used to construct antisense sequences to control the expression of the coding sequence of interest.

Optionally, agents identified in any of the above-described assays may be confirmed as useful in modulating region-specific DNA demethylation, neurogenesis, neuroprotective activity, or neuronal plasticity, by any standard in vitro assay (e.g., those described herein) or in any standard animal model (e.g., a rodent model of depression, ischemic injury). In one embodiment, the agents are assayed for DNA demethylation activity using a methylation-sensitive restriction enzyme (e.g., McrBC), by direct immunostaining of 5-methylcytosine, by chromatin immunoprecipitation (ChIP), or methylated DNA immunoprecipitation (MeDIP). In other embodiments, activity of a Gadd45b-dependent demethylation pathway is assayed.

In other embodiments, agents are characterized as promoting Gadd45-dependent neuronal plasticity by measuring dendritic complexity, dendritic length, or synapse formation. In other embodiments, Gadd45-dependent neurogenesis is assayed, for example, using BrdU. In still other embodiments, Gadd45-dependent neuroprotective activity is assayed by measuring a reduction in cell death in a cell having a propensity to undergo cell death (e.g., following an ischemic insult). In other embodiments, Gadd45b-dependent promotion of neuronal regeneration is assayed by measuring nerve growth.

Small molecules of the invention preferably have a molecular weight below 2,000 daltons, more preferably between 300 and 1,000 daltons, and most preferably between 400 and 700 daltons. It is preferred that these small molecules are organic molecules.

Test Agents and Extracts

In general, agents capable of modulating region-specific DNA demethylation, enhancing neural plasticity, enhancing neurogenesis, or useful as a neuroprotectant (e.g., by promotomg neuronal survival), or to treat a mood disorder, such as depression, are identified from large libraries of both natural product or synthetic (or semi-synthetic) extracts or chemical libraries according to methods known in the art. Those skilled in the field of drug discovery and development will understand that the precise source of test extracts or agents is not critical to the procedure(s) of the invention. Accordingly, virtually any number of chemical extracts or agents can be screened using the methods described herein. Examples of such extracts or agents include, but are not limited to, plant-, fungal-, prokaryotic- or animal-based extracts, fermentation broths, and synthetic agents, as well as modification of existing agents. Numerous methods are also available for generating random or directed synthesis (e.g., semi-synthesis or total synthesis) of any number of chemical agents, including, but not limited to, saccharide-, lipid-, peptide-, and nucleic acid-based agents. Synthetic agent libraries are commercially available from Brandon Associates (Merrimack, N.H.) and Aldrich Chemical (Milwaukee, Wis.). Alternatively, libraries of natural agents in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or agent is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity should be employed whenever possible.

When a crude extract is found to have a desired activity (e.g., Gadd45 binding activity) further fractionation of the positive lead extract is necessary to isolate chemical constituents responsible for the observed effect. Thus, the goal of the extraction, fractionation, and purification process is the careful characterization and identification of a chemical entity within the crude extract having activity. Methods of fractionation and purification of such heterogenous extracts are known in the art. If desired, agents shown to be useful to modulate region-specific DNA demethylation, enhance neurogenesis, having neuroprotective activity, or enhancing neuronal plasticity, may be assayed by any standard assay (e.g., those described herein) are chemically modified according to methods known in the art.

Polynucleotide Therapy

Polynucleotide therapy featuring a polynucleotide encoding a Gadd45 protein, variant, or fragment thereof is another therapeutic approach for treating a disease characterized by the dysregulation of DNA demethylation. Expression of such proteins in a neuronal cell is expected to promote survival of the cell, for example, by reducing cell death, to increase neurogenesis, to increase neuroplasticity, or to prevent or treat a mood disorder, such as depression. Gadd45 nucleic acid molecules can be delivered to cells of a subject requiring modulation of region specific DNA demethylation. The nucleic acid molecules must be delivered to the cells of a subject in a form in which they can be taken up so that therapeutically effective levels of a Gadd45 protein or fragment thereof can be produced.

Transducing viral (e.g., retroviral, adenoviral, and adeno-associated viral) vectors can be used for somatic cell therapy, especially because of their high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272: 263-267, 1996; and Miyoshi et al., Proc. Natl. Acad. Sci. U.S.A. 94:10319, 1997). For example, a polynucleotide encoding a Gadd45 protein, variant, or a fragment thereof, can be cloned into a retroviral vector and expression can be driven from its endogenous promoter, from the retroviral long terminal repeat, or from a promoter specific for a target cell type of interest. Other viral vectors that can be used include, for example, a vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:775-83S, 1995). Retroviral vectors are particularly well developed and have been used in clinical settings (Rosenberg et al., N. Engl. J. Med 323:370, 1990; Anderson et al., U.S. Pat. No. 5,399,346). In one preferred embodiment, a viral vector is used to administer a Gadd45 polynucleotide to a neuronal cell.

Non-viral approaches can also be employed for the introduction of a therapeutic to a cell of a patient requiring Gadd45 DNA demethylation activity. For example, a Gadd45 nucleic acid molecule can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263: 14621, 1988; Wu et al., Journal of Biological Chemistry 264:16985, 1989), or by micro-injection under surgical conditions (Wolff et al., Science 247:1465, 1990). Preferably the Gadd45 nucleic acids are administered in combination with a liposome and protamine.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. Transplantation of normal genes into the affected tissues of a patient can also be accomplished by transferring a normal Gadd45 nucleic acid into a cultivatable cell type ex vivo (e.g., an autologous or heterologous primary cell or progeny thereof), after which the cell (or its descendants) are injected into a targeted tissue.

cDNA expression for use in polynucleotide therapy methods can be directed from any suitable promoter (e.g., the human cytomegalovirus (CMV), simian virus 40 (SV40), or metallothionein promoters, or neuron specific promoters), and regulated by any appropriate mammalian regulatory element. For example, if desired, enhancers known to preferentially direct gene expression in specific cell types (e.g., neurons) can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

Another therapeutic approach included in the invention involves administration of a recombinant therapeutic, such as a recombinant a Gadd45 protein, variant, or fragment thereof, either directly to the site of a potential or actual disease-affected tissue or systemically (for example, by any conventional recombinant protein administration technique). The dosage of the administered protein depends on a number of factors, including the size and health of the individual patient. For any particular subject, the specific dosage regimes should be adjusted over time according to the individual need and the professional judgment of the person administering or supervising the administration of the compositions.

Inhibitory Nucleic Acids

Inhibitory nucleic acid molecules are those oligonucleotides that inhibit the expression or activity of a Gadd45 polypeptide. Such oligonucleotides are useful for reducing Gadd45 in a cell having excessive Gadd45 expression or activity (e.g., undesired DNA demethylation). Such oligonucleotides include single and double stranded nucleic acid molecules (e.g., DNA, RNA, and analogs thereof) that bind a nucleic acid molecule that encodes a c Gadd45 rystallin polypeptide (e.g., antisense molecules, siRNA, shRNA) as well as nucleic acid molecules that bind directly to a Gadd45 polypeptide to modulate its biological activity (e.g., aptamers).

Ribozymes

Catalytic RNA molecules or ribozymes that include an antisense Gadd45 sequence of the present invention can be used to inhibit expression of a Gadd45 nucleic acid molecule in vivo. The inclusion of ribozyme sequences within antisense RNAs confers RNA-cleaving activity upon them, thereby increasing the activity of the constructs. The design and use of target RNA-specific ribozymes is described in Haseloff et al., Nature 334:585-591. 1988, and U.S. Patent Application Publication No. 2003/0003469 A1, each of which is incorporated by reference.

Accordingly, the invention also features a catalytic RNA molecule that includes, in the binding arm, an antisense RNA having between eight and nineteen consecutive nucleobases. In preferred embodiments of this invention, the catalytic nucleic acid molecule is formed in a hammerhead or hairpin motif. Examples of such hammerhead motifs are described by Rossi et al., Aids Research and Human Retroviruses, 8:183, 1992. Example of hairpin motifs are described by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, Biochemistry, 28:4929, 1989, and Hampel et al., Nucleic Acids Research, 18: 299, 1990. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

Small hairpin RNAs consist of a stem-loop structure with optional 3' UU-overhangs. While there may be variation, stems can range from 21 to 31 bp (desirably 25 to 29 bp), and the loops can range from 4 to 30 bp (desirably 4 to 23 bp). For expression of shRNAs within cells, plasmid vectors containing either the polymerase III H1-RNA or U6 promoter, a cloning site for the stem-looped RNA insert, and a 4-5-thymidine transcription termination signal can be employed. The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs. Additional methods for expressing the shRNA in mammalian cells are described in the references cited above.

siRNA

Short twenty-one to twenty-five nucleotide double-stranded RNAs are effective at down-regulating gene expression (Zamore et al., Cell 101: 25-33; Elbashir et al., Nature 411: 494-498, 2001, hereby incorporated by reference). The therapeutic effectiveness of an sirNA approach in mammals was demonstrated in vivo by McCaffrey et al. (Nature 418: 38-39.2002).

Given the sequence of a target gene, siRNAs may be designed to inactivate that gene. Such siRNAs, for example, could be administered directly to an affected tissue, or administered systemically. The nucleic acid sequence of an Gadd45 gene can be used to design small interfering RNAs (siRNAs). The 21 to 25 nucleotide siRNAs may be used, for example, as therapeutics to treat a vascular disease or disorder.

The inhibitory nucleic acid molecules of the present invention may be employed as double-stranded RNAs for RNA interference (RNAi)-mediated knock-down of Gadd45 expression. In one embodiment, Gadd45 expression is reduced in a neuronal cell. RNAi is a method for decreasing the cellular expression of specific proteins of interest (reviewed in Tuschl, Chembiochem 2:239-245, 2001; Sharp, Genes & Devel. 15:485-490, 2000; Hutvagner and Zamore, Curr. Opin. Genet. Devel. 12:225-232, 2002; and Hannon, Nature 418:244-251, 2002). The introduction of siRNAs into cells either by transfection of dsRNAs or through expression of siRNAs using a plasmid-based expression system is increasingly being used to create loss-of-function phenotypes in mammalian cells.

In one embodiment of the invention, double-stranded RNA (dsRNA) molecule is made that includes between eight and nineteen consecutive nucleobases of a nucleobase oligomer of the invention. The dsRNA can be two distinct strands of RNA that have duplexed, or a single RNA strand that has self-duplexed (small hairpin (sh)RNA). Typically, dsRNAs are about 21 or 22 base pairs, but may be shorter or longer (up to about 29 nucleobases) if desired. dsRNA can be made using standard techniques (e.g., chemical synthesis or in vitro transcription). Kits are available, for example, from Ambion (Austin, Tex.) and Epicentre (Madison, Wis.). Methods for expressing dsRNA in mammalian cells are described in Brummelkamp et al. Science 296:550-553, 2002; Paddison et al. Genes & Devel. 16:948-958, 2002. Paul et al. Nature Biotechnol. 20:505-508, 2002; Sui et al. Proc. Natl. Acad. Sci. USA 99:5515-5520, 2002; Yu et al. Proc. Natl. Acad. Sci. USA 99:6047-6052, 2002; Miyagishi et al. Nature Biotechnol. 20:497-500, 2002; and Lee et al. Nature Biotechnol. 20:500-505 2002, each of which is hereby incorporated by reference.

Small hairpin RNAs consist of a stem-loop structure with optional 3' UU-overhangs. While there may be variation, stems can range from 21 to 31 bp (desirably 25 to 29 bp), and the loops can range from 4 to 30 bp (desirably 4 to 23 bp). For expression of shRNAs within cells, plasmid vectors containing either the polymerase III H1-RNA or U6 promoter, a cloning site for the stem-looped RNA insert, and a 4-5-thymidine transcription termination signal can be employed. The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs. Additional methods for expressing the shRNA in mammalian cells are described in the references cited above.

Delivery of Inhibitory Nucleic Acid Molecules

Naked inhibitory nucleic acid molecules, or analogs thereof, are capable of entering mammalian cells and inhibiting expression of a gene of interest. Nonetheless, it may be desirable to utilize a formulation that aids in the delivery of oligonucleotides or other nucleobase oligomers to cells (see, e.g., U.S. Pat. Nos. 5,656,611, 5,753,613, 5,785,992, 6,120, 798, 6,221,959, 6,346,613, and 6,353,055, each of which is hereby incorporated by reference).

Pharmaceutical Therapeutics

The invention provides a simple means for identifying agents (including peptides, small molecule inhibitors, and mimetics) capable of modulating Gadd45 polypeptide or polynucleotide activity. Accordingly, a chemical entity discovered to have medicinal value using the methods described herein is useful as a drug or as information for structural modification of existing agents, e.g., by rational drug design.

For therapeutic uses, the compositions or agents identified using the methods disclosed herein may be administered systemically, for example, formulated in a pharmaceutically-acceptable buffer such as physiological saline. Treatment may be accomplished directly, e.g., by treating the animal with agents which modulate region-specific DNA demethylation, enhance neural plasticity, enhance neurogenesis, act as a neuroprotectant (e.g., to promote neuronal survival), or to treat a mood disorder, such as depression. Preferable routes of administration include, for example, subcutaneous, intravenous, interperitoneally, intramuscular, or intradermal injections which provide continuous, sustained levels of the drug in the patient. Treatment of human patients or other animals will be carried out using a therapeutically effective amount of an agent in a physiologically-acceptable carrier. Suitable carriers and their formulation are described, for example, in Remington's Pharmaceutical Sciences by E. W. Martin. The amount of the agent to be administered varies depending upon the manner of administration, the age and body weight of the patient, and with the type of disease and extensiveness of the disease. Generally, amounts will be in the range of those used for other agents used in the treatment of other diseases, although in certain instances lower amounts will be needed because of the increased specificity of the agent. An agent is administered at a dosage that modulates region-specific DNA demethylation, enhances neural plasticity, enhances neurogenesis, acts as a neuroprotectant (e.g., promotes neuronal survival or reduces cell death), or treats a mood disorder, such as depression. If desired, such treatment is also performed in conjunction with standard therapies.

Therapy

The invention features compositions and methods that are useful for modulating the expression or biological activity of Gadd45 in neurons. In certain embodiments, methods for increasing Gadd45 expression or activity are useful for promoting neurogenesis, promoting neural plasticity, promoting neuronal survival or reducing cell death (e.g., having neuroprotective activity) or useful for the treatment of mood disorders, such as depression.

In other embodiments, the invention provides methods for reducing Gadd45 expression or biological activity. Such methods are useful for the treatment of conditions associated with dysregulated Gadd45 expression. For example, subjects with autism have been characterized as having undesirably high levels of neuronal Gadd45 expression (Garbett et al., Neurobiol Dis. 2008 June; 30(3):303-11. Epub 2008 Mar. 10). Accordingly, the invention provides methods for reducing Gadd45 levels in such subjects for the treatment of autism and other conditions characterized by undesirable levels of Gadd45 expression. In another example, subjects with mental retardation were found to have undesirably high levels of Gadd45 expression (Tarpet et al., Nat Genet. 2007 September; 39(9):1127-33. Epub 2007 Aug. 19). Accordingly, the invention provides compositions and methods for the treatment of subjects with mental retardation associated with undesirably increased levels of Gadd45 expression.

Therapy may be provided wherever clinical therapies are typically performed, e.g., at home, the doctor's office, a clinic, a hospital's outpatient department, or a hospital. Treatment generally begins at a hospital so that the doctor can observe the therapy's effects closely and make any adjustments that are needed. The duration of the therapy depends on the kind of disease being treated, the age and condition of the patient, the stage and type of the patient's disease, and how the patient's body responds to the treatment. Drug administration may be performed at different intervals (e.g., daily, weekly, or monthly).

A Gadd45 modulator is administered within a pharmaceutically-acceptable diluent, carrier, or excipient, in unit dosage form. Conventional pharmaceutical practice may be employed to provide suitable formulations or compositions to administer the compounds to patients suffering from a disease that is caused by excessive cell proliferation. Administration may begin before the patient is symptomatic. Any appropriate route of administration may be employed, for example, administration may be parenteral, intravenous, intraarterial, subcutaneous, intratumoral, intramuscular, intracranial, intraorbital, ophthalmic, intraventricular, intrahepatic, intracapsular, intrathecal, intracisternal, intraperitoneal, intranasal, aerosol, suppository, or oral administration. For example, therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" Ed. A. R. Gennaro, Lippincourt Williams & Wilkins, Philadelphia, Pa., 2000. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for Gadd45 modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The formulations can be administered to human patients in therapeutically effective amounts (e.g., amounts which prevent, eliminate, or reduce a pathological condition) to provide therapy for a disease or condition. The preferred dosage of a Gadd45 nucleobase oligomer of the invention is likely to depend on such variables as the type and extent of the disorder, the overall health status of the particular patient, the formulation of the compound excipients, and its route of administration.

The present invention provides methods of treating disease and/or disorders or symptoms thereof which comprise administering a therapeutically effective amount of a pharmaceutical composition comprising a compound of the formulae herein to a subject (e.g., a mammal such as a human). Thus, one embodiment is a method of treating a subject suffering from or susceptible to a neuronal disease or disorder or symptom thereof. The method includes the step of administering to the mammal a therapeutic amount of an amount of a compound herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which region-specific DNA demethylation may be implicated.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with Gadd45, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Adult neurogenesis represents a prominent form of structural plasticity through continuous generation of new neurons in the mature mammalian brain. Similar to other neural activity-induced plasticity with fine structural changes within individual neurons, adult neurogenesis is modulated by a plethora of external stimuli. For example, synchronized activation of mature dentate neurons by electroconvulsive treatment (ECT) in adult mice causes sustained up-regulation of hippocampal neurogenesis (T. M. Madsen et al., *Biol Psychiatry* 47, 1043 (2000)) without any detectable cell damage (FIGS. 1A and 1B). How transient activation of mature neuronal circuits modulates adult neurogenesis over days and weeks is largely unknown.

Example 1

Gadd45b is Induced by Electroconvulsive Therapy

Epigenetic mechanisms potentially provide a basis for such long-lasting modulation. The expression profiles of known epigenetic regulators in response to ECT were examined, including those involved in chromatin modification. One gene found to be strongly induced by ECT was Gadd45b (FIG. 2A), a member of the Gadd45 family previously implicated in DNA repair, adaptive immune response (H. J. Jung et al., *Oncogene* 26, 7517 (2007); H. Tran et al., *Science* 296, 530 (2002); M. C. Hollander, A. J. Fornace, Jr., *Oncogene* 21, 6228 (2002); B. Lu, A. F. Ferrandino, R. A. Flavell, *Nat Immunol* 5, 38 (2004)), and DNA 5-methylcytosine excision in cultured cells (G. Barreto et al., *Nature* 445, 671 (2007)). Gadd45b induction was characterized by neuronal activity in the adult hippocampus. Analysis of micro-dissected dentate gyrus tissue showed robust, transient induction of Gadd45b expression by a single ECT (FIG. 2A; FIG. 3; Table 1).

TABLE 1

Primer sequences used in quantitative real-time
PCR analysis of genomic DNA, mRNA, bisulfite sequencing,
ChIP analysis and methylation-specific PCR.

mRNA expression analysis

| Genes | 5' primer | 3' primer |
| --- | --- | --- |
| Gadd45b | GTTCTGCTGCGACAATGACA | TTGGCTTTTCCAGGAATCTG |
| Gadd45a | TGCGAGAACGACATCAACAT | TCCCGGCAAAAACAAATAAG |
| Gadd45g | ATGACTCTGGAAGAAGTCCGT | CAGGGTCCACATTCAGGACT |
| BDNF-IV | CAGGAGTACATATCGGCCACC | TGGTCATCACTCTTCTCACCTG |
| BDNF-IX | GCAGCTGGAGTGGATCAGTAA | TGGTCATCACTCTTCTCACCTG |
| Total BDNF | GCCTTTGGAGCCTCCTCT | CTGTCACACACGCTCAGCTC |
| FGF-1B | GAGAGGCAGCTTCAGTCCAG | TCACAAGACGGGAATGAAGTC |
| Total FGF-1 | GCGGTCCTCGGACTCACTA | AGCCAATGGTCAAGGGAAC |
| Arc | AGCGGGACCTGTACCAGAC | AGCTGCTCCAGGGTCTTG |

Methylation IP and ChIP analysis

| Regions | 5' primer | 3' primer |
| --- | --- | --- |
| Oct4 | AAGGCTAGAGGGTGGGATTG | CGAAGTCTGAAGCCAGGTGT |
| SINE-B1 | TGGTGGTGGTTGAGACAGC | TAGTGGCACACACCTTTAATCC |
| SINE-B2 | GGCTGGTGAGATGGCTCAGT | TACACTGTAGCTGTCTTCAGACA |
| BDNF-IV | TTCGAGGCAGAGGAGGTATC | TTCAGCGAGAAGCTCCATTT |
| BDNF-IX | CATGAGACCGGGCAAGTC | CCTTGGGAGGAATGTGTGAT |
| FGF-1B | CTGATGAGCAAGGGCCAAG | TCACAAGACGGGAATGAAGTC |
| FGF-1G | TTTGCAGAGGACACCGATAG | ACCCGTCTACACCACACACA |
| FGF-2 | ATGGCTGCCAGCGGCATC | TGGATGCGCAGGAAGAAG |

Bisulfite sequencing analysis

| Regions | 5' primer | 3' primer |
| --- | --- | --- |
| BDNF-IX | TTGGAAATAAGTAAAATTTTTATAGATGT | TCAAATCAACAACATAATCCTTAAAAAAA |
| FGF-1B | TTTTGTTGATGAGTAAGGGTTAAGG | CAAACTAAAAAACTCTCTTCACTCCA |
| FGF-1G | TAGAAGGTAGGTTTGTAGAGGATAT | ACCACACACACCAAATCAAATATTA |
| Oct4 | TGGGTTGAAATATTGGGTTTATTT | CTAAAACCAAATATCCAACCATA |

Methylation-specific PCR analysis (FGF-1B)

| Allele | 5' primer | 3' primer |
| --- | --- | --- |
| Methylated (M) | GTAGATTTGGAGGTTAGCGTTTTC | TAAAATCCGCTAAACAACCTTTACG |
| Un-methylated (UM) | GGTAGATTTGGAGGTTAGTGTTTTTG | AAATAAAATCCACTAAACAACCTTTACAC |

Example 2

Physiological Stimulation Induced Gadd45b Expression

Figure 2:
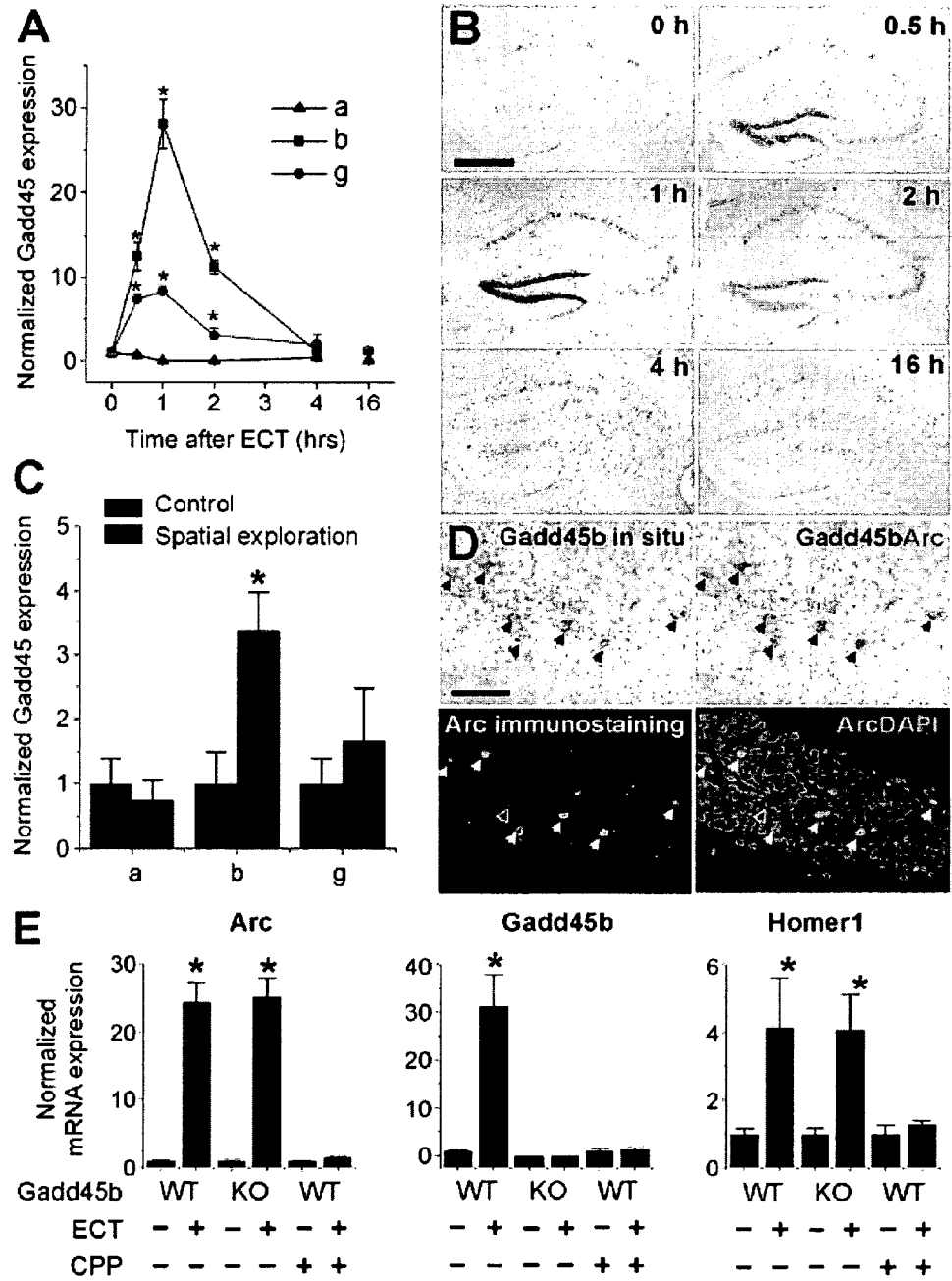
FIGS. 2A-2E show that activity induced neuronal Gadd45b expression.
Figure 3:
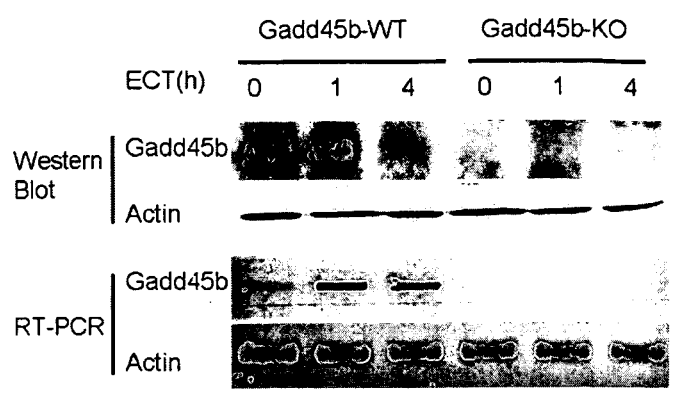
FIG. 3 shows that ECT-induced Gadd45b mRNA and protein expression in the dentate gyrus of the adult mouse hippocampus. Microdissected dentate gyrus tissue from adult WT and KO mice without ECT and at 1 or 4 hrs after a single ECT was subjected to Western blot analysis using anti-Gadd45b serum or to Q-PCR analysis (top panel). β-actin was used as the loading control. Note the specificity of antibodies and PCR primers for Gadd45b as determined by the absence of signals from the KO mice (bottom panel).
Figure 4:
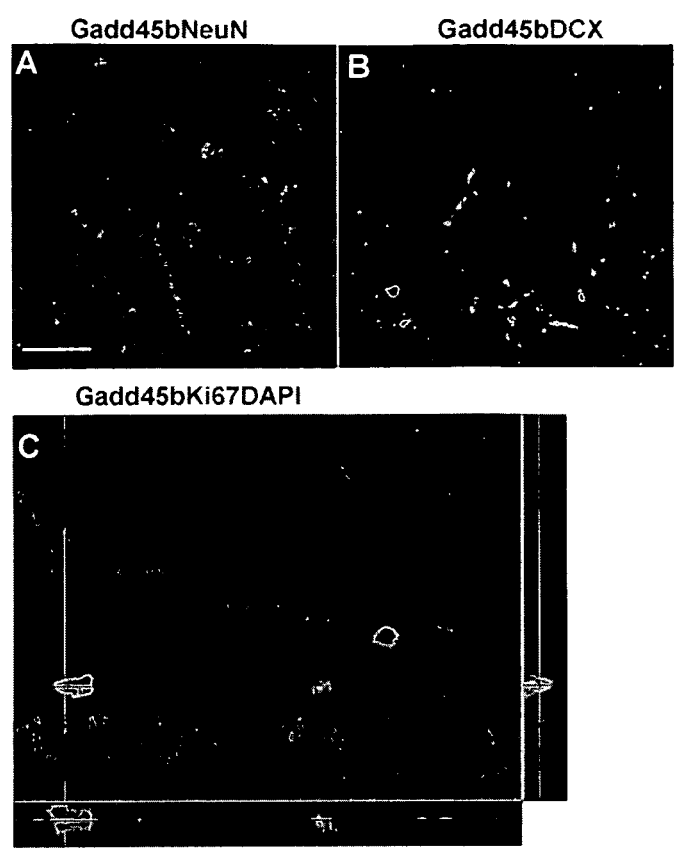
FIGS. 4A-4C show induction of Gadd45b expression in mature dentate granule cells of the adult mouse hippocampus after ECT. Adult animals were subjected to a single ECT and processed 1 hr later for in situ hybridization analysis of Gadd45b mRNA and immunostaining of NeuN, a mature neuronal marker (FIG. 4A), DCX, an immature neuronal marker (FIG. 4B), or Ki67, a cell proliferation marker (FIG. 4C). Shown are sample confocal images of Gadd45b in situ hybridization, and NeuN, DCX or Ki67 immunostaining. Orthogonal view is also shown in (C) to verify the non-overlapping distribution of the Gadd45b in situ signal (red) and Ki67 immunostaining signal (green). Scale bar: 20 µm.
Figure 5:
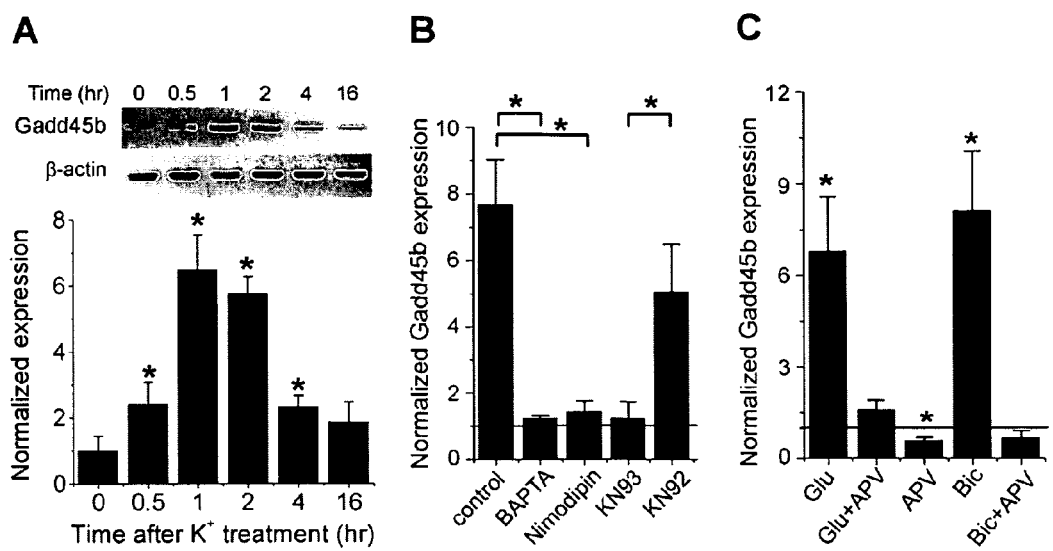
FIG. 5A-5C show regulation of Gadd45b expression in cultured primary hippocampal neurons.

In situ analysis revealed induction largely in NeuN+ mature dentate granule cells (FIG. 2B; FIGS. 4A-4C). Spatial exploration of novel environment, a behavioral paradigm that activates immediate early genes (IEGs) (V. Ramirez-Amaya et al., *J Neurosci* 25, 1761 (2005)), also led to significant induction of Gadd45b, but not Gadd45a or Gadd45g (FIG. 2, C-D). The majority of Gadd45b-positive cells also expressed Arc (FIG. 2D; 88±3%; n=4), a classic activity-induced IEG. Thus, physiological stimulation is sufficient to induce Gadd45b expression in dentate granule cells. Experiments with pharmacological manipulations of primary hippocampal neurons further suggested that Gadd45b induction by activity requires the N-methyl D-aspartate receptor (NMDAR), $Ca^{2+}$, and CaMK signaling (FIG. 5)

Example 3

Signal Transduction Mechanism Underlying Activity-Induced Neuronal Gadd45b Expression To delineate mechanisms underlying activity-induced Gadd45b expression, primary hippocampal neurons in culture were used. Depolarization of neurons with elevated $K^+$ (50 mM) led to a significant increase of Gadd45b expression, with a time-course similar to those with ECT in vivo (FIG. 5A). The induction was abolished by the $Ca^{2+}$ chelator BAPTA (50 μM), the voltage-gated $Ca^{2+}$ channel blocker Nimodipin (10 μM), and the CaM kinase inhibitor KN93 (10 μM), but not by the inactive analog KN92 (10 μM; FIG. 5B). Gadd45b expression was also induced by glutamate (20 μM) and blocked by the NMDAR antagonist APV (200 μM; FIG. 5C). Interestingly, application of APV alone significantly decreased Gadd45b expression, whereas the $GABA_AR$ antagonist bicuculline (50 μM) had the opposite effect (FIG. 5C). Thus, endogenous excitatory synaptic activity is sufficient to drive Gadd45b expression. Together with the in vivo evidence (FIG. 2E), these results indicate that Gadd45b shares the same classic induction pathway as other activity-induced immediate early genes (West et al., Nat Rev Neurosci 3, 921 (2002). Chen et al., J Neurobiol 64, 4 (2005)). In vivo injection of the NMDAR antagonist CPP abolished ECT-induced Gadd45b and Arc expression in the adult dentate gryus (FIG. 2E). Taken together, these results indicate that Gadd45b shares the same induction pathway as classic activity-induced IEGs (S. W. Flavell, M. E. Greenberg, *Annu Rev Neurosci* 31, 563 (2008)).

Figure 6:
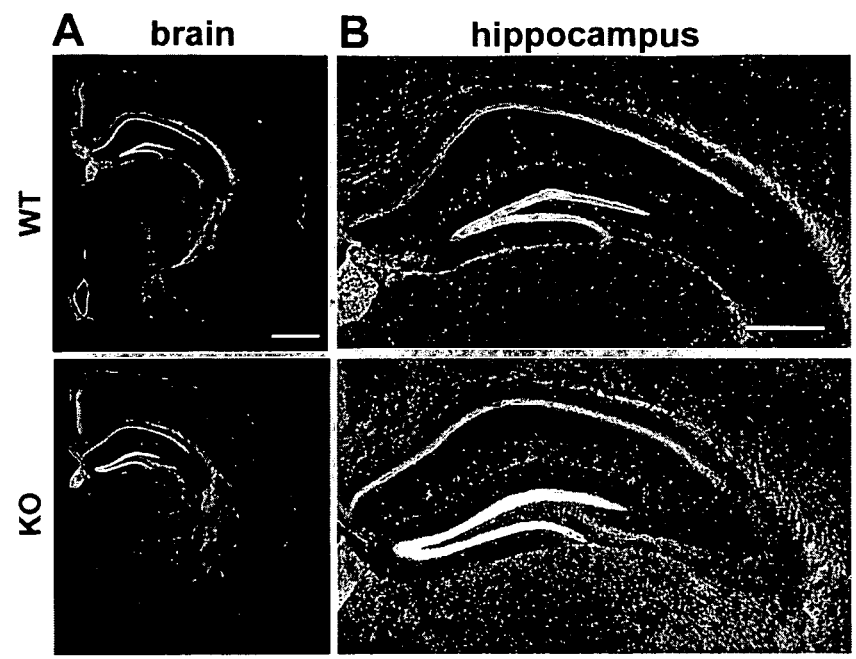
FIGS. 6A and 6B are confocal images showing the normal cytoarchitectural structure in the cortex and hippocampus of adult Gadd45b WT and KO mice. Shown are sample confocal images of DAPI staining of the brain (FIG. 6A) and the hippocampus (FIG. 6B). Scale bars: 1 mm for (FIG. 6A) and 0.5 mm for (FIG. 6B).
Figure 7:
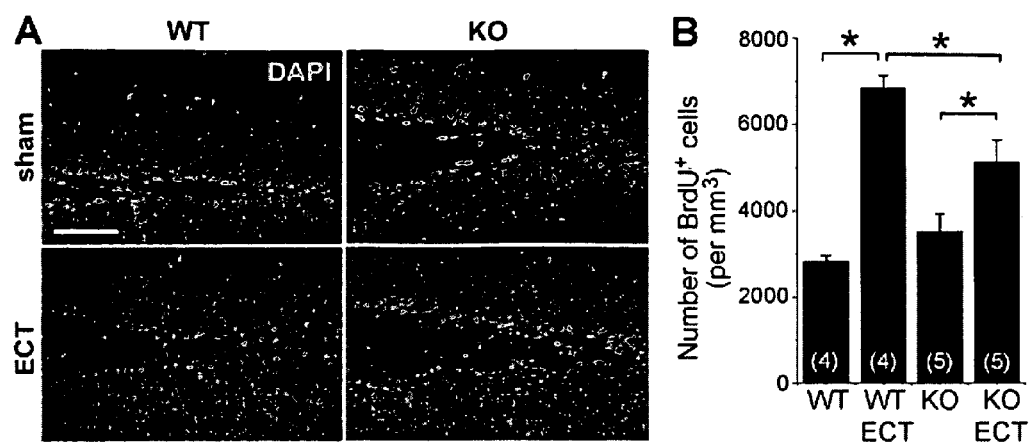
FIGS. 7A and 7B show the role of Gadd45b in activity-induced proliferation of adult neural progenitors.
Figure 8:
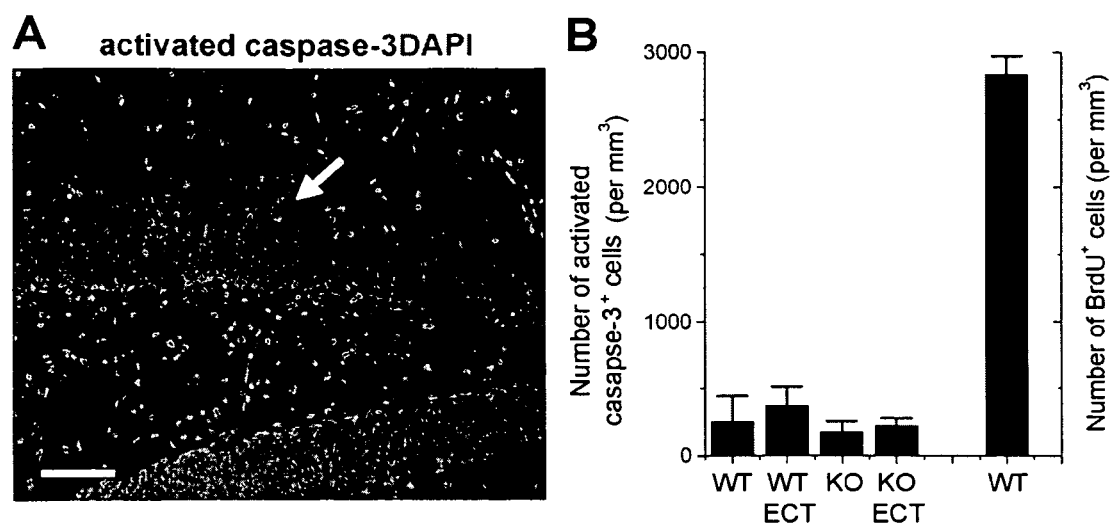
FIGS. 8A and 8B show that no significant cell death occurred in the dentate gyrus of adult mice under different experimental conditions.
Figure 9:
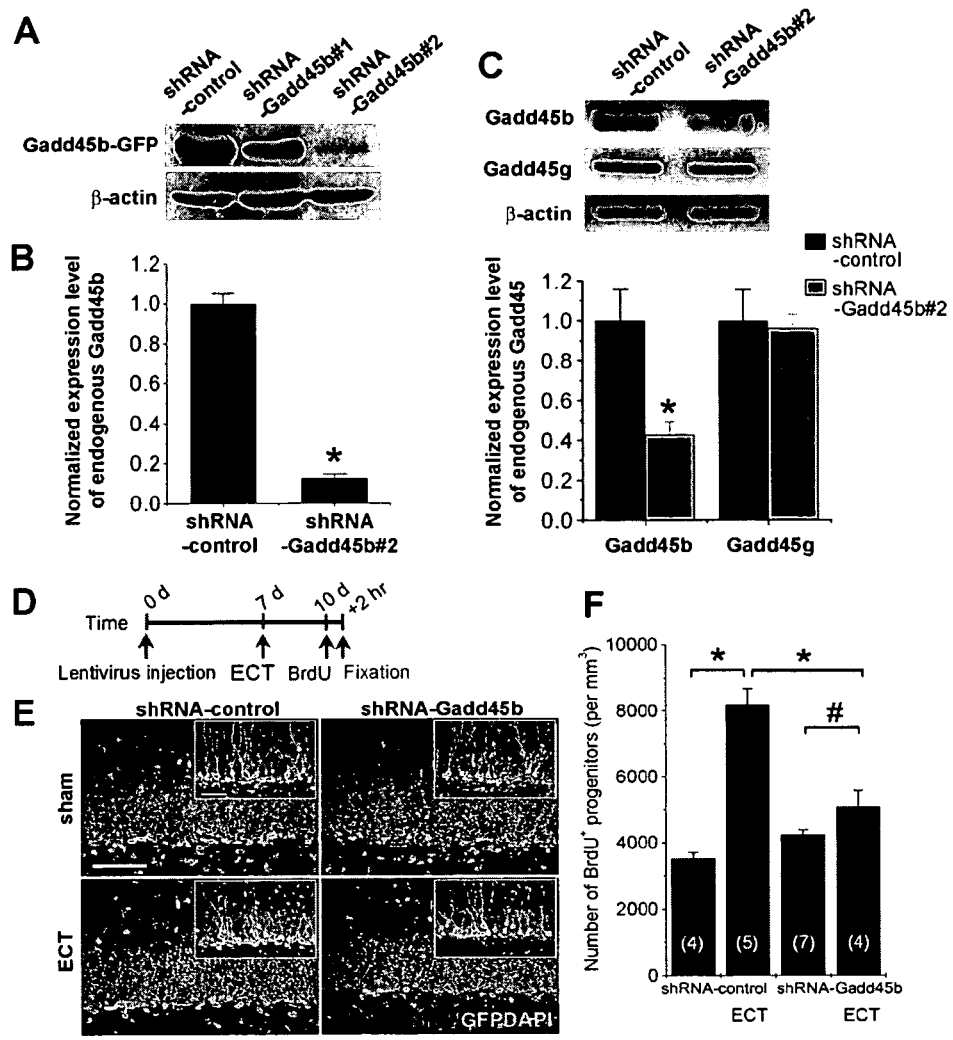
FIGS. 9A-9F show the effects of acute Gadd45b knock-down on ECT-induced proliferation of adult neural progenitors.
Figure 10:
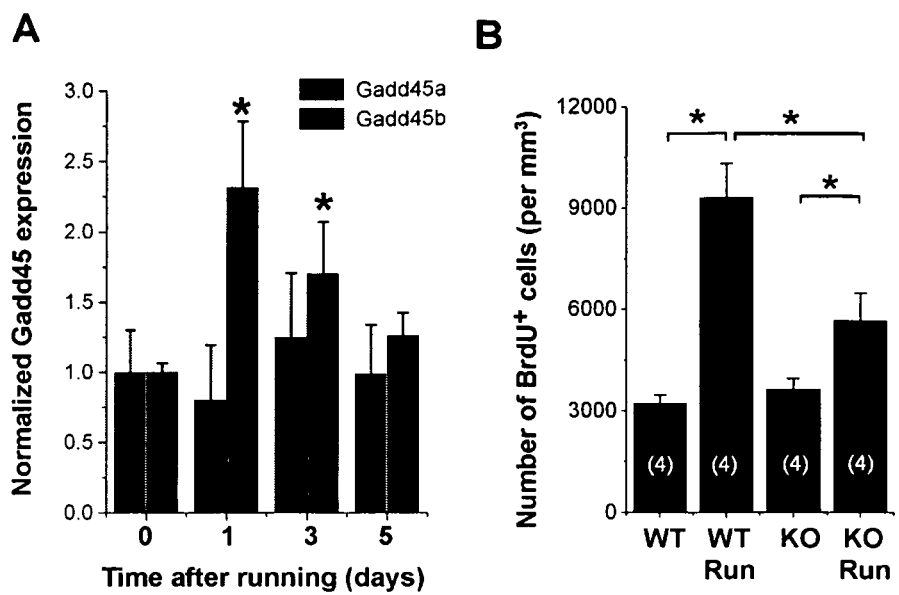
FIGS. 10A and 10B are graphs showing the role of Gadd45b in running-induced proliferation of neural progenitors in the dentate gyrus of adult mice. Littermates of adult Gadd45b WT and KO mice were housed in normal cage or with free access to a running wheel. (A) Summary of Gadd45a and Gadd45b expression. Controls and experimental groups were processed in parallel at different time points after the start of running and micro-dissected dentate gyrus tissue was used for Q-PCR analysis. Values were normalized to those of β-actin for each sample and then normalized to the control at the time 0. Values represent mean±SEM (n=3 animals; *: P<0.01, ANOVA).

Example 4 shRNA-Gadd45b Abolished ECT-Induced Proliferation of Adult Neural Progenitors Next it was assessed whether Gadd45b induction is required for neural activity-dependent adult neurogenesis. Adult Gadd45b knockout (KO) (Lu et al., *Nat Immunol* 5, 38 (2004)) mice appeared anatomically normal (FIG. 6) and exhibited identical NMDAR-dependent induction of known IEGs at 1 hr after ECT (FIG. 2E). To examine neural progenitor proliferation, adult mice at 3 days after ECT or sham treatment were injected with bromodeoxyuridine (BrdU) and sacrificed 2 hrs later. Stereological counting showed similar densities of BrdU+ cells in the dentate gyrus between WT and KO mice without ECT (FIG. 7). After ECT, however, there was a 140% increase in the density of BrdU+ cells in WT mice with only 40% increase in KO littermates (FIG. 7). Little caspase-3 activation was detected within the dentate gyrus under all these conditions (FIG. 1; FIG. 8), ruling out a potential contribution from cell death. To confirm this finding with a manipulation of better spatiotemporal control, lentiviruses were developed to knockdown the expression of endogenous Gadd45b with short-hairpin RNA (shRNA; FIG. 9 Expression of shRNA-Gadd45b through stereotaxic viral injection largely abolished ECT-induced proliferation of adult neural progenitors, whereas the basal level was similar to that of shRNA-control (FIG. 9). Exercise-induced adult neurogenesis also induced a modest Gadd45b elevation (FIG. 10A). A 7-day running program led to a dramatic increase of neural progenitor proliferation in adult WT mice, but was significantly less effective in their KO littermates (FIG. 10B). Taken together, these results demonstrate a specific and essential role of Gadd45b in activity-induced, but not basal level of neural progenitor proliferation in the adult dentate gyrus.

Example 5

Figure 11:
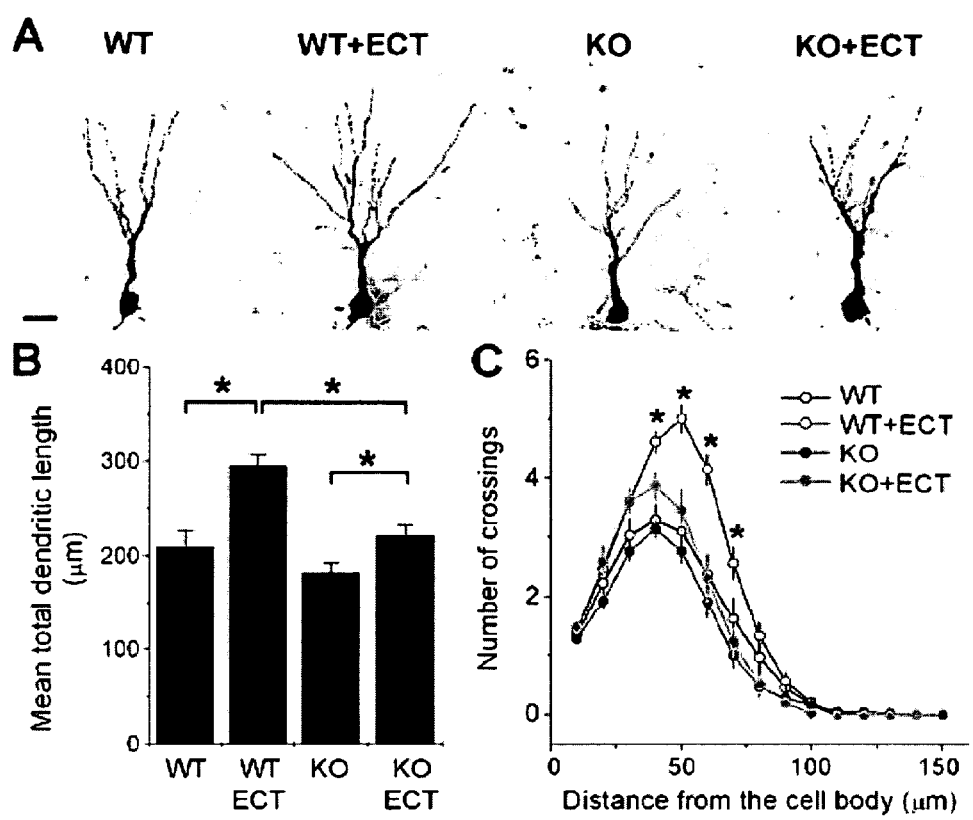
FIGS. 11A-11C show the role of Gadd45b in activity-induced dendritic development of newborn neurons in the adult brain.

Gadd45b Mediates Activity-Induced Dendritic Development of Newborn Neurons in the Adult Brain The role of Gadd45b induction in the dendritic development of newborn neurons was examined. Retroviruses expressing GFP were stereotaxically injected into the dentate gyrus of adult WT and KO mice to label proliferating neural progenitors and their progeny (S. Ge et al., *Nature* 439, 589 (2006)). A single ECT was given at 3 days after injection, when the majority of GFP-labeled cells were already postmitotic neurons (S. Ge et al., *Nature* 439, 589 (2006)). Quantitative analysis showed that ECT led to a marked increase in the total dendritic length and complexity of GFP+ newborn neurons at 14 days after retroviral labeling (FIGS. 11A-11C). This ECT-induced dendritic growth was significantly attenuated in KO mice, while the basal level of dendritic growth was similar (FIGS. 11A-11C). Thus, Gadd45b functions in activity-induced dendritic development of newborn neurons in the adult brain.

Figure 12:
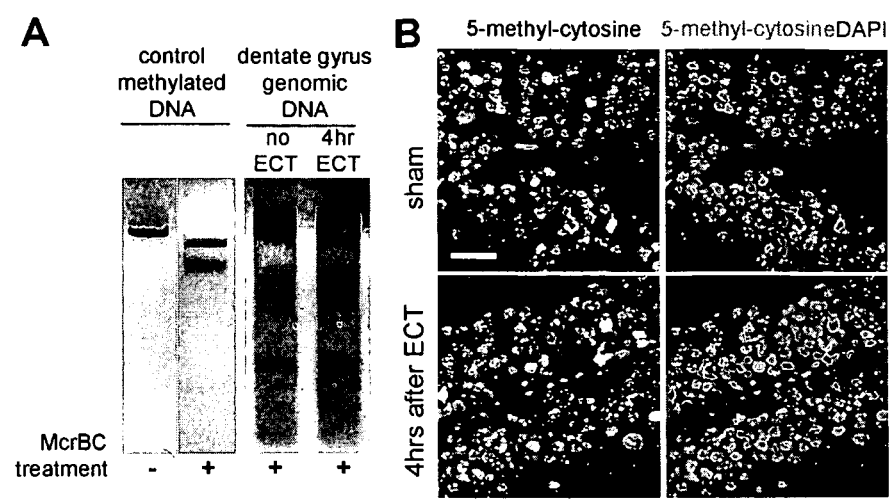
FIGS. 12A and 12B show a lack of global DNA demethylation in the dentate gyrus of the adult brain after ECT.
Figure 13:
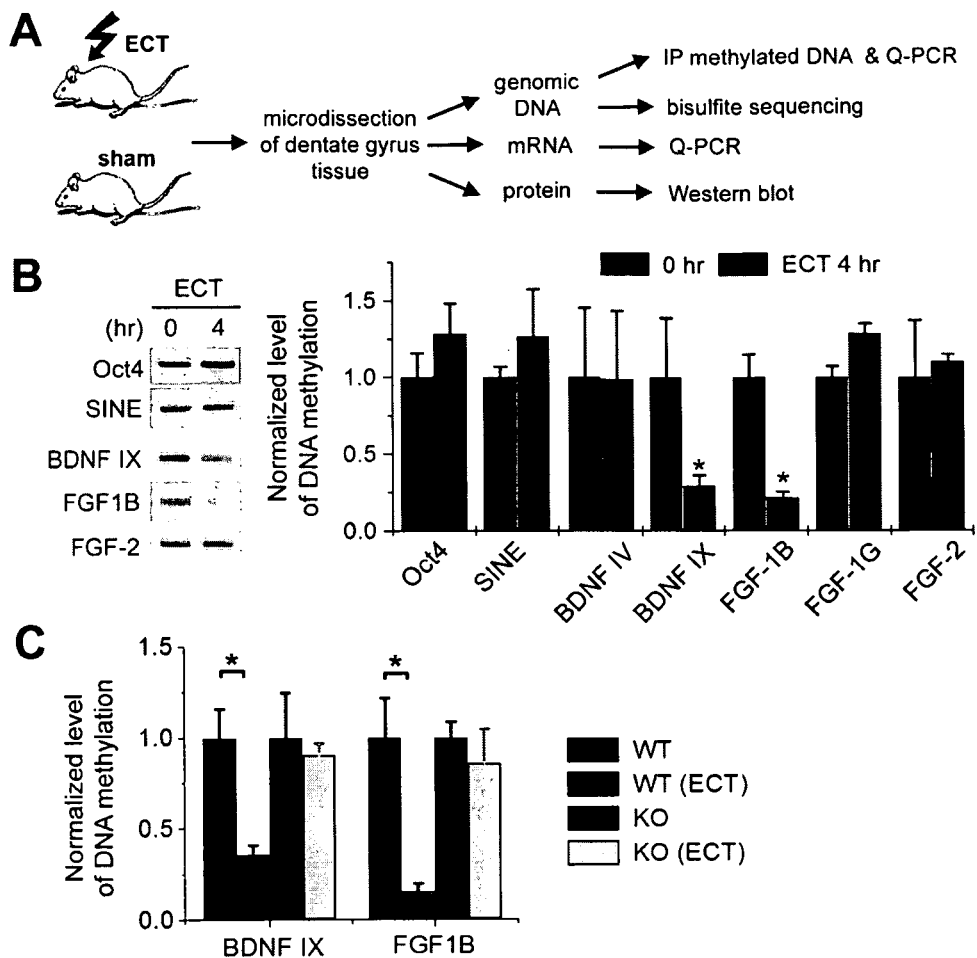
FIGS. 13A-13C shows that Gadd45b regulates ECT-induced demethylation of specific regulatory regions in the dentate gyrus of the adult brain.

How does transient Gadd45b induction regulate activity-dependent adult neurogenesis over the long-term? Gadd45a has been implicated in promoting global DNA demethylation in cultured cells, yet the finding remains controversial (G. Barreto et al., *Nature* 445, 671 (2007), S. G. Jin, C. Guo, G. P. Pfeifer, *PLoS Genet* 4, e1000013 (2008)). To examine whether Gadd45b induction may confer long-lasting epigenetic modulation in the expression of neurogenic niche signals, DNA methylation status was analyzed using micro-dissected adult dentate tissue enriched in NeuN+ mature neurons. No significant global DNA demethylation was detected after ECT in vivo (FIGS. 12 and 13).

Example 6

Demethylation was Found at Specific Regulatory Regions Involved in Neurogenesis Analysis of genomic DNA from micro-dissected adult mouse dentate gyrus tissue treated with methylation-sensitive restriction enzyme McrBC (FIG. 12A) and direct immunostaining of 5-methylcytosine in dentate granule cells (FIG. 12B) showed no detectable differences between sham controls and at 4 hrs after ECT. Methylated DNA immunoprecipitation (MeDIP) analysis also showed no differences in the DNA methylation level at several genomic loci (FIG. 13B), including the pluripotent cell-specific gene Oct4 regulatory region and short interspersed repetitive elements (SINE), which have been used to estimate the global DNA methylation status. Thus, no significant global DNA demethylation occurs in adult dentate gyrus after Gadd45b induction by ECT.

Methylated DNA immunoprecipitation (MeDIP) analysis was used in a preliminary screen for region-specific DNA demethylation, with a focus on growth factor families that have been implicated in regulating adult neurogenesis (G. L. Ming, H. Song, *Annu Rev Neurosci* 28, 223 (2005)). Significant demethylation was found at specific regulatory regions of brain-derived neurotrophic factor (BDNF) and fibroblast growth factor-1 (FGF-1; FIG. 13B). Bisulfite sequencing analysis further confirmed ECT-induced demethylation within the regulatory region IX of BDNF (T. Aid, A. Kazantseva, M. Piirsoo, K. Palm, T. Timmusk, *J Neurosci Res* 85, 525 (2007)) and the brain-specific promoter B of FGF-1 (K. Y. Alam et al., *J Biol Chem* 271, 30263 (1996)) (FIG. 14A-B; FIGS. 15A and 15B; Table 2).

TABLE 2

List of P-values for ANOVA analysis of DNA methylation levels in individual alleles (same data set as shown in FIG. 4B).

|  | WT vs. WT + ECT | KO vs. KO + ECT | WT vs. KO | WT + ECT vs. KO + ECT |
| --- | --- | --- | --- | --- |
| BDNF-IX | 0.0002 (**) | 0.58 | 0.47 | 0.029 (*) |
| FGF-1B | 0.0004 () | 0.16 | 0.34 | 0.004 () |
| FGF-1G | 0.56 | N/A | N/A | N/A |
| Oct4 | 0.83 | N/A | N/A | N/A |

Figure 14:
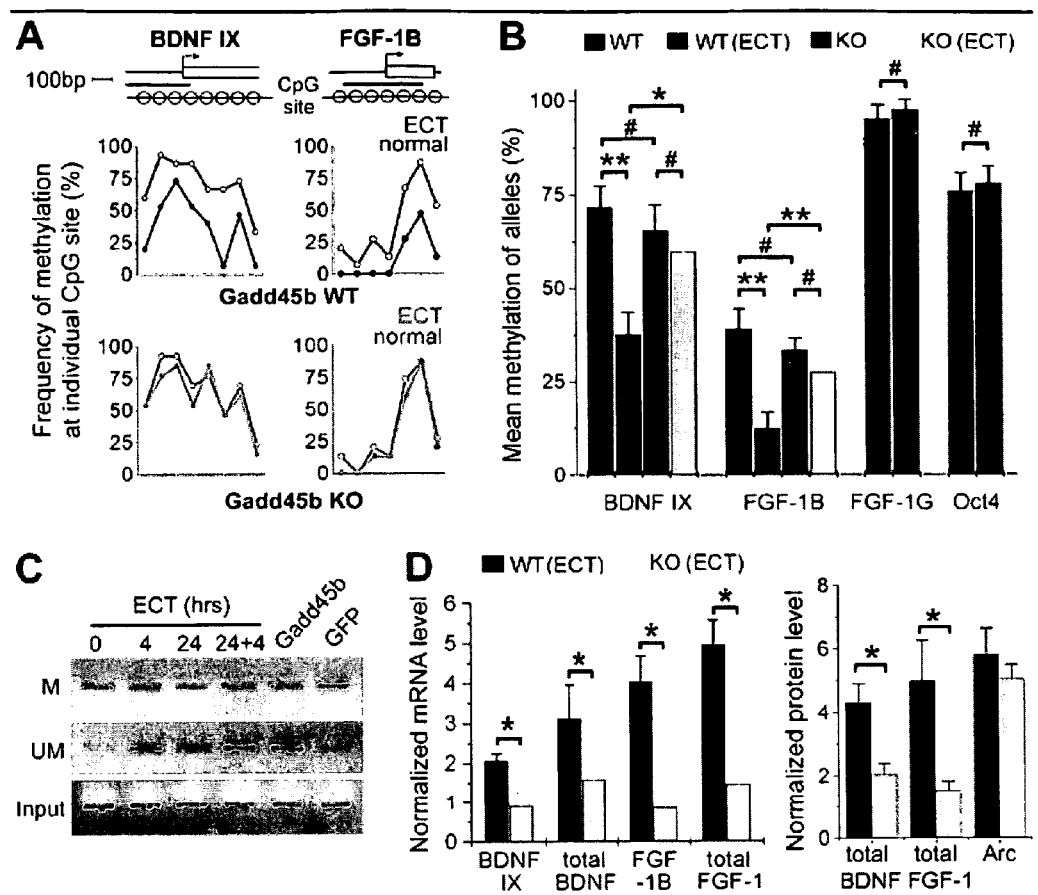
FIGS. 14A-14C show the role of Gadd45b in activity-induced specific DNA demethylation and gene expression in the adult dentate gyrus.
FIG. 14D is a graph that summarizes the mRNA and protein expression in the dentate gyrus of adult Gadd45b WT and KO mice at 4 hrs after ECT and sham controls. Values represent mean± SEM (n=4; *: P<0.01, ANOVA).
Figure 15:
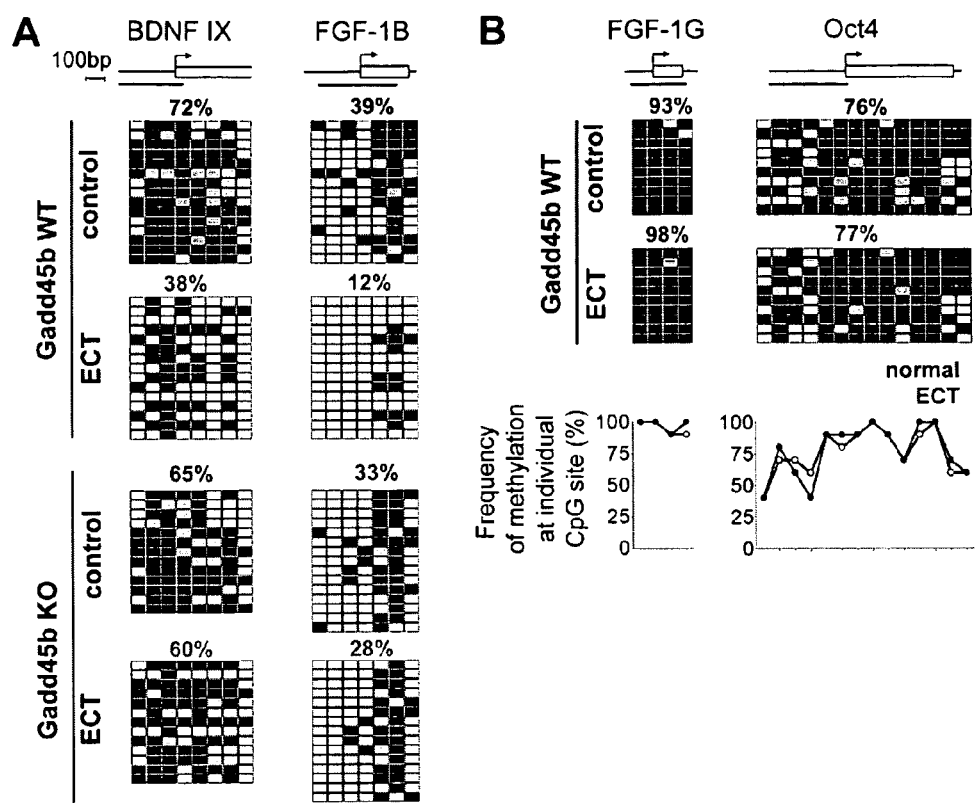
FIGS. 15A and B shows results of bisulfite sequencing analysis of the methylation status of specific regulatory regions in the adult dentate gyrus before or at 4 hrs after ECT.
FIG. 15B (bottom panel) shows a summary of methylation frequency at individual CpG sites.
Figure 16:
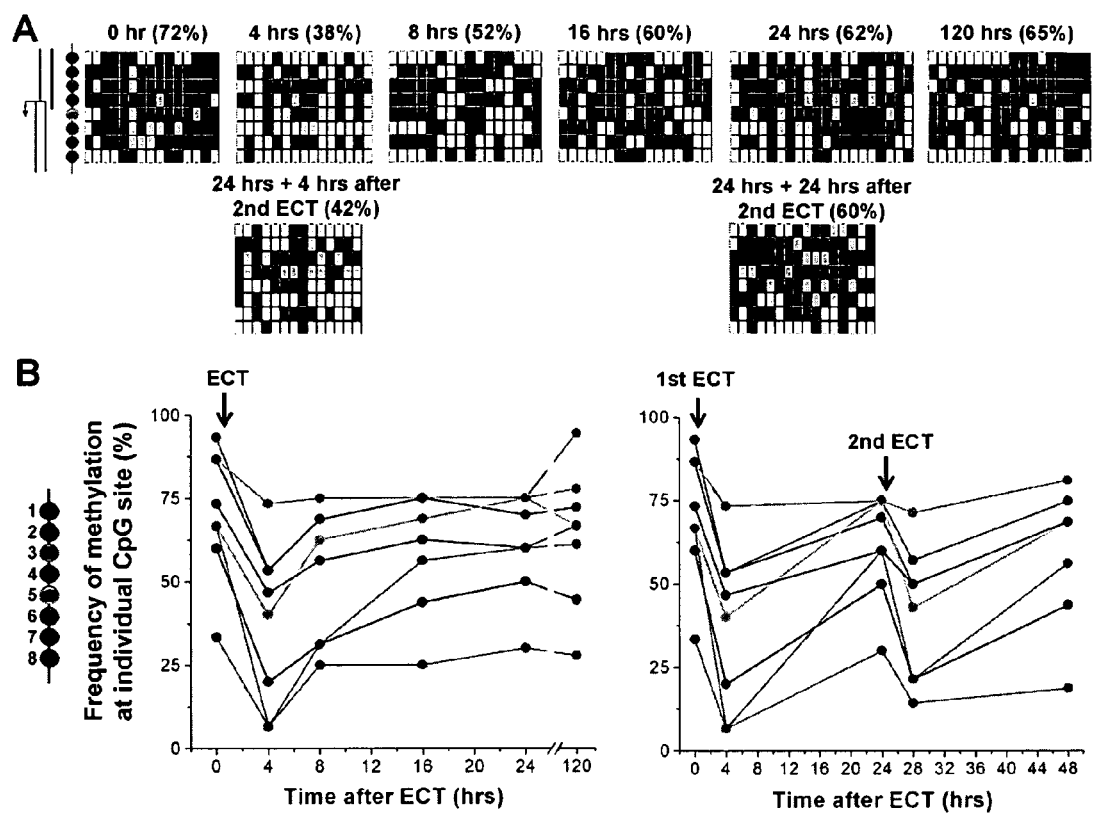
FIGS. 16A and 16B show the dynamics of DNA demethylation and re-methylation of CpG sites within the BDNF-XI regulatory region after ECT. Genomic DNA from micro-dissected dentate gyrus tissue of WT animals at different time points after a single ECT or a second ECT at 24 hrs after the first ECT was subjected to bisulfite sequencing analysis of specific genomic regions within the BDNF-IX regulatory region.
Figure 17:
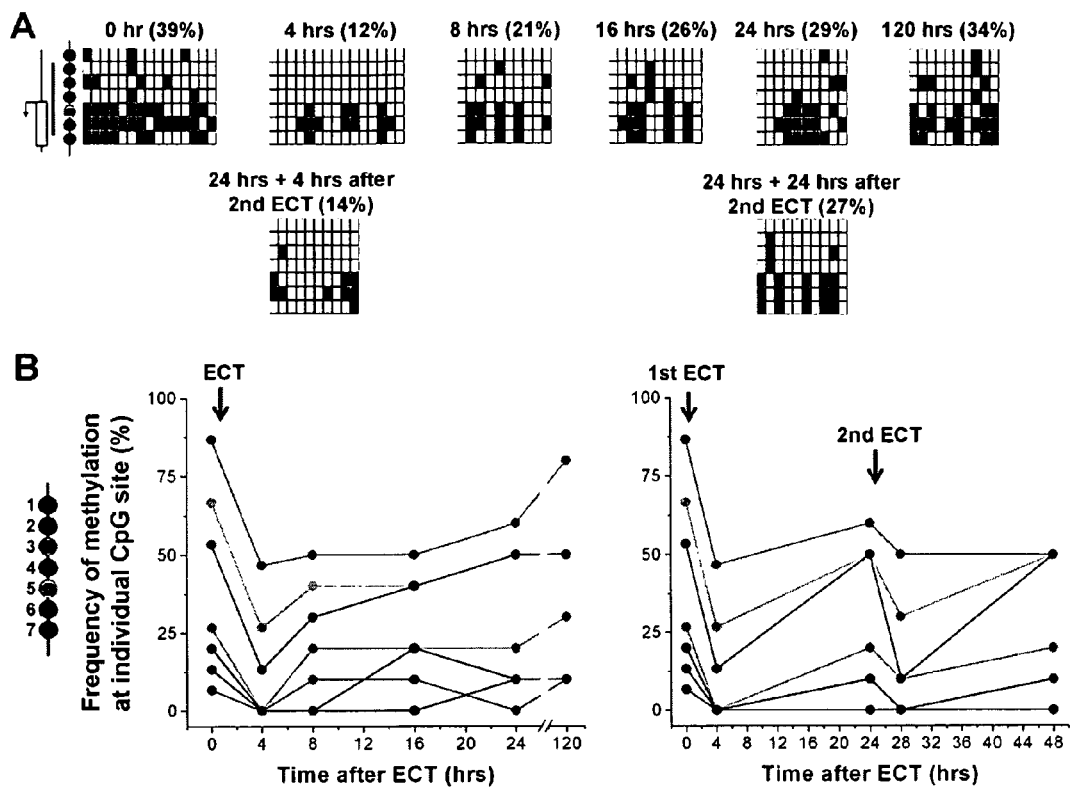
FIGS. 17A and 17B show the dynamics of DNA demethylation and re-methylation of CpG sites within the FGF1-B regulatory region after ECT. Genomic DNA from microdissected dentate gyrus tissue of WT animals at different time points after a single ECT or a second ECT at 24 hrs after the first ECT was subjected to bisulfite sequencing analysis of specific genomic regions within the FGF1-B regulatory region.
Figure 18:
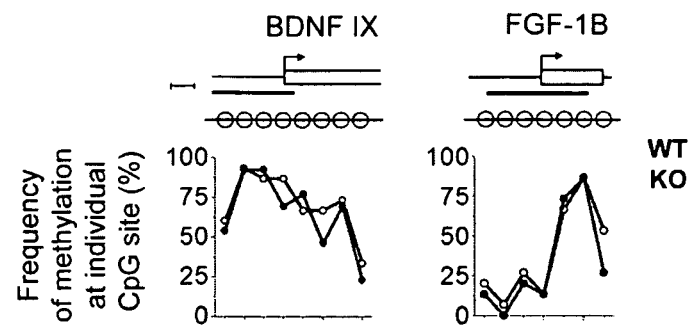
FIG. 18 shows a comparison of the methylation status of individual CpG sites in regulatory regions for selected genes in the dentate gyrus of Gadd45b WT and KO mice without ECT. On the top is a schematic diagram showing the genomic region subjected to bisulfite sequencing analysis relative to the transcriptional start site. Scale bar: 100 bp. Shown below is a summary plot of the frequency of methylation at individual CpG sites from WT and KO mice. Note no differences in the methylation levels at individual sites between WT and KO mice in the examined regions.
Figure 19:
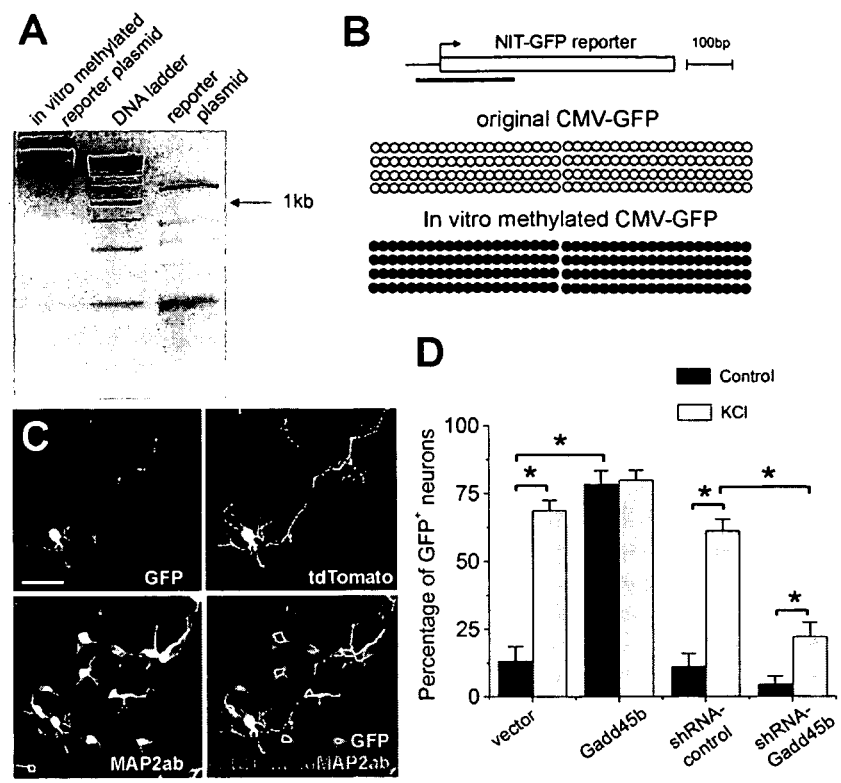
FIGS. 19A-19D show that Gadd45b promotes expression from methylation-silenced reporter plasmids in post-mitotic neurons. GFP reporter plasmids were methylated in vitro using bacterial CpG methyltransferase SssI. The completeness of methylation was confirmed by full protection from HpaII digestion (FIG. 19A) and by bisulfite sequencing (FIG. 19B). Primary hippocampal neurons in culture were co-transfected with these in vitro methylated GFP reporter plasmids and control vectors expressing tdTomato, vectors co-expressing tdTomato and Gadd45b, or vectors co-expressing tdTomato and control or shRNA against Gadd45b. Cultures were treated with medium or KCl at 24 hrs after transfection. The expression of GFP and tdTomato was analyzed 2 days later.
Figure 20:
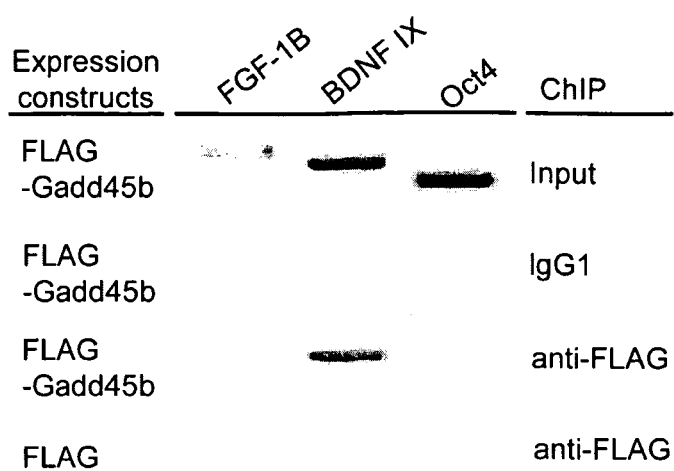
FIG. 20 is a Western blot. A neuronal chromatin immuno-precipitation demonstrated specific and direct binding of Gadd45b to its target regulatory regions. E18 primary hippocampal neuronal cultures were electroporated with control FLAG or FLAG-Gadd45b expression constructs before plating and were subjected to chromatin IP after 7 days in vitro using antibodies specific to FLAG. Specific primers for FGF-1B, BDNF IX and Oct4 regulatory regions were used in PCR (See Table 1). Note the specific presence of regulatory regions of FGF-1B and BDNF IX, but not Oct4, in FLAG-Gadd45b bound chromatin fractions.
Figure 21:
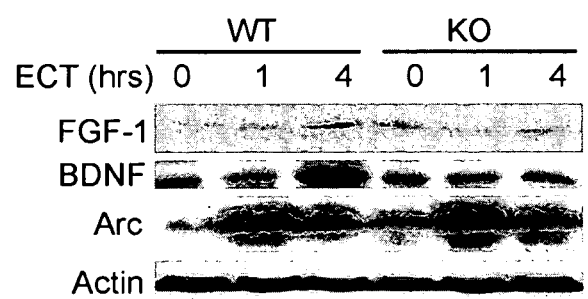
FIG. 21 is a Western blot showing that ECT-induced protein expression in the dentate gyrus of adult Gadd45b WT and KO mice. Microdissected dentate gyrus tissues from WT or KO mice at 4 hrs after ECT or sham controls were subjected to Western blot analysis. Actin was used as the loading control.

Every CpG site within these regions exhibited marked reduction in the frequency of methylation (FIG. 14A). Time-course analysis further revealed the temporal dynamics of DNA methylation status at these CpG sites (FIGS. 16 and 17). In contrast, no significant change was induced by ECT in the pluripotent cell specific Oct4 promoter or the kidney and liver-specific FGF-1G promoter (18) (FIG. 14B; FIG. 15B). Comparison of adult Gadd45b WT and KO mice without ECT showed no significant difference in the basal levels of DNA methylation within BDNF IX and FGF-1B regulatory regions (FIG. 14B; FIG. 18). In contrast, ECT-induced DNA demethylation of these regions was almost completely abolished in KO mice (FIG. 14A-B; FIG. 14C; FIG. 15A). In addition, overexpression of Gadd45b appeared to promote DNA demethylation in vivo (FIG. 14C) and to activate methylation-silenced reporters in cultured post-mitotic neurons (FIGS. 19A-19D). Chromatin immunoprecipitation (ChIP) analysis further showed specific binding of Gadd45b to the FGF-1B and BDNF IX regulatory regions (FIG. 20). ECT-induced gene expression from these regions and total expression of BDNF and FGF-1, were largely absent in Gadd45b KO mice at 4 hrs (FIG. 14D; FIG. 21), consistent with a critical role of DNA methylation status in regulating gene expression. Thus, Gadd45b is essential for activity-dependent demethylation and late-onset expression of specific secreted factors in the adult dentate gyrus.

Figure 22:
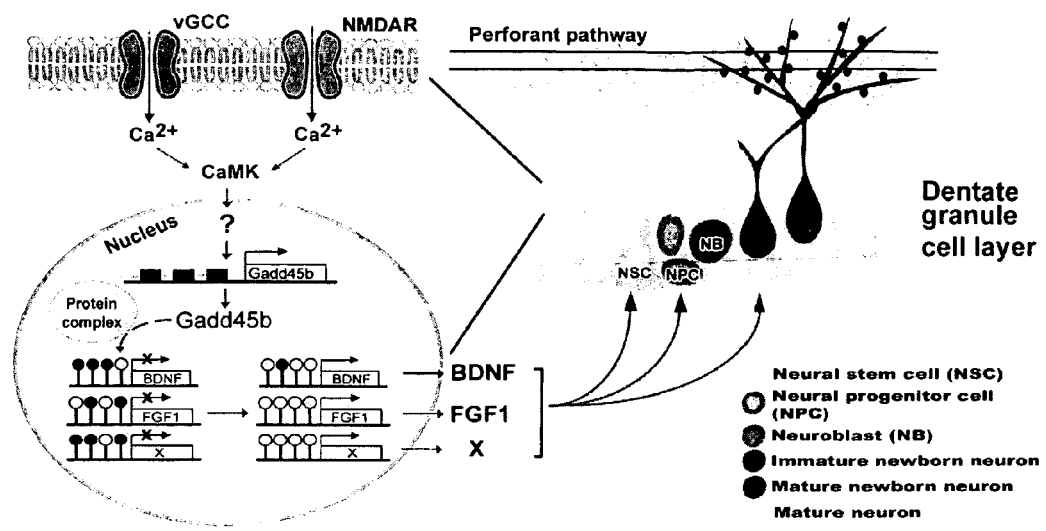
FIG. 22 is a schematic diagram that provides a model of Gadd45b signaling and function in neural activity-induced adult neurogenesis. Transient activation of mature dentate granule cells induces Gadd45b expression through an NMDAR-$Ca^{2+}$-CaM kinase pathway. Gadd45b triggers activation of a protein demethylation complex, leading to increased expression of specific target genes in mature neurons, including BDNF and FGF1. Secreted extrinsic factors from mature neurons in turn promote several key aspects of adult neurogenesis over the long-term.

In summary, Gadd45b links neuronal circuit activity to region-specific DNA demethylation and expression of paracrine neurogenic niche factors from mature neurons in controlling key aspects of activity-dependent adult neurogenesis (FIG. 22).

Example 7

Non Cell-Autonomous Roles of Gadd45b in Regulating Activity-Dependent Adult Neurogenesis Activity-induced Gadd45b is predominantly expressed in NeuN$^+$ mature dentate granule cells (FIGS. 2B and 4) and there were very few Gadd45b$^+$Ki67$^+$ cells in the adult dentate gyrus at 1 hr after ECT (2.2% of all Ki67$^+$ cells examined; FIG. 4C). These results are consistent with early reports that activity-induced expression of immediate early genes, such as c-Fos, Arc or Zif268, only in new neurons older than 15 days (Cervoni, M. Szyf, *J Biol Chem* 276, 40778 (2001)) and strongly suggests that Gadd45b deletion affects predominantly, if not exclusively, mature neurons. It is possible that Gadd45b may be induced by activity in new neurons during later phase of development or by developmental program independent of neural activity. Collectively, current evidence supports a non-cell autonomous role of neuronal Gadd45b induction in extrinsic modulation of activity-dependent early-stage adult neurogenesis (FIG. 22).

Figure 23:
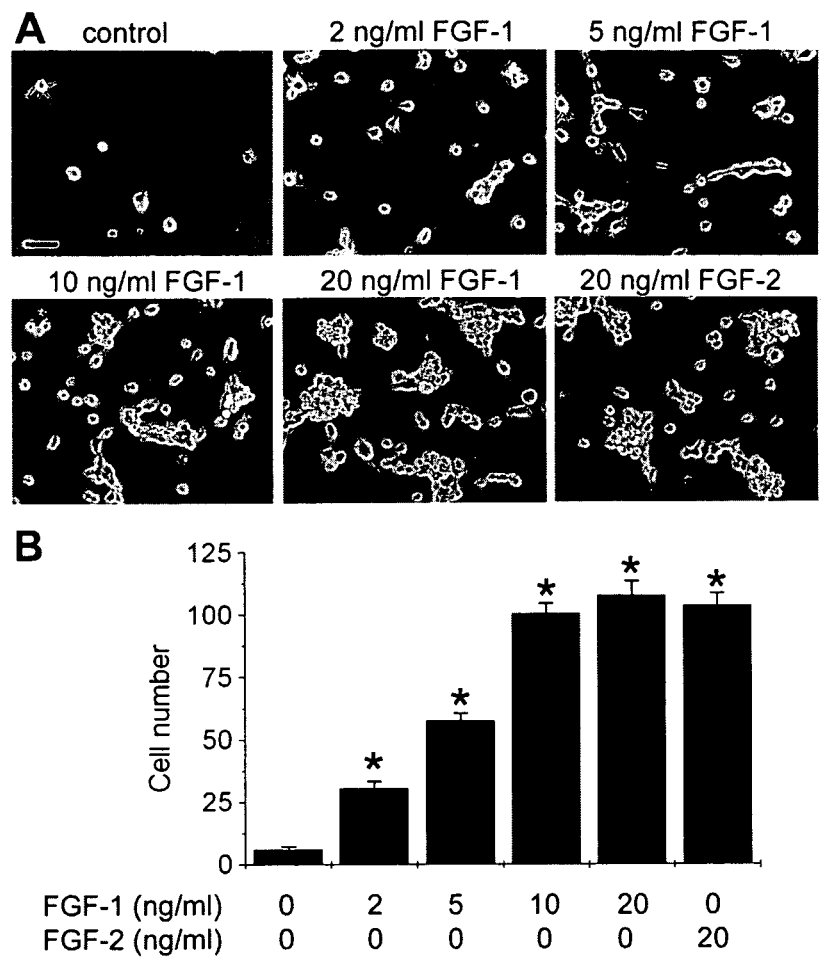
FIGS. 23A and 23B are micrographs and a graph, respectively, showing that FGF-1 promotes proliferation of adult neural progenitors in culture.

As endogenous targets of Gadd45b-dependent demethylation pathway, BDNF is known to promote dendritic growth of neurons in vivo and FGF-1 exhibited robust mitogenic activity as FGF-2 on neural progenitor proliferation in vitro (FIG. 23). The presence of Gadd45b in chromatin associated with BDNF IX and FGF-1B regulatory regions in neurons (FIG. 20) points to its direct role in gene regulation and potentially in a demethylation complex (FIG. 22) (N. Cervoni, M. Szyf, *J Biol Chem* 276, 40778 (2001)). The known role of Gadd45 family in 5-methylcytosine excision is consistent with the emerging notion that region-specific demethylation can be mediated through DNA repair-like mechanisms as supported by genetic and biochemical studies in both *Arabidopsis* and mammalian cells.

Genetic evidence from *Arabidopsis* and biochemical studies suggest that 5-methylcytosine demethylation can be mediated through mechanisms similar to DNA nucleotide or base excise repair. Although it remains unlikely that such a mechanism would mediate global DNA demethylation, it may be well-suited for gene-specific local demethylation. Gadd45 family proteins have been implicated in both DNA nucleotide and base excision repair. Gadd45a KO cells are deficient in the base excision repair (Jung et al., *Oncogene* 26, 7517 (2007)) and recombinant Gadd45a protein stimulates DNA excision repair in vitro (Smith et al., *Science* 266, 1376 (1994)).

More recently, over-expression of Gadd45a has been shown to promote active DNA demethylation in cell culture and reduced level of Gadd45a causes defects of DNA methylation pattern in specific tumor suppressor genes (Barreto et al., *Nature* 445, 671 (2007)). Such active demethylation appears to occur through DNA repair-like mechanisms and Gadd45a interacts with and requires the DNA repair endonuclease XPG (Barreto et al., *Nature* 445, 671 (2007)). In addition to its direct involvement in repair-like demethylase complex, Gadd45b may also oligomerize (Kovalsky et al., *J Biol Chem* 276, 39330 (2001) and relax chromatin to promote gene accessibility for demethylation through interactions with acetylated histones (Carrier et al., *Mol Cell Biol* 19, 1673 (1999); Cervoni, M. Szyf, *J Biol Chem* 276, 40778 (2001).

Recruitment of Gadd45b to specific genomic loci may also be mediated by acetylated histone and/or various transcription factors. From a combination of multiple approaches, the data reported herein indicates that inducible Gadd45b functions as a rate-limiting regulator for highly gene-specific, active DNA demethylation pathway in neurons (FIG. 22).

Gadd45b may trigger activation of a demethylation pathway comprising protein machinery for chromatin remodelling and DNA repair-like excision complexes. The effects of Gadd45b are highly gene-specific in vivo according to different external stimuli and cellular contexts.

How transient neuronal activation achieves long-lasting effects in neural plasticity and memory has been a long-standing question; enzymatic modification of cytosine in DNA was proposed as a means to provide such necessary stability with reversibility (R. Holliday, *J Theor Biol* 200, 339 (1999)). Although DNA demethylation can occur passively during cell division, emerging evidence suggests the existence of active demethylation in post-mitotic cells (K. Martinowich et al., Science 302, 890 (2003); I. C. Weaver et al., Nat Neurosci 7, 847 (2004); F. D. Lubin, T. L. Roth, J. D. Sweatt, J Neurosci 28, 10576 (2008)). DNA demethylation in neurons represents an extra layer of activity-dependent regulation, in addition to transcription factors and histone-modifying enzymes. Gadd45b expression is altered in some autistic patients (K. Garbett et al., *Neurobiol Dis* 30, 303 (2008).) and is induced by light in the suprachiasmatic nucleus (V. M. Porterfield, H. Piontkivska, E. M. Mintz, *BMC Neurosci* 8, 98 (2007)), and by induction of long-term potentiation in vivo (D. Hevroni et al., *J Mol Neurosci* 10, 75 (1998)). Gadd45b is also associated with critical period plasticity in the visual cortex (M. Majdan, C. J. Shatz, *Nat Neurosci* 9, 650 (2006)). Thus, Gadd45b may represent a common target of physiological stimuli in different neurons in vivo and mechanisms involving epigenetic DNA modification are likely important for activity-dependent neural plasticity.

The results reported herein were carried out using the following methods and materials.

Animals and Stimulation with ECT, Spatial Exploration of Novel Environment and Running Adult (6-8 weeks old) Gadd45b WT and KO mice in the C57BL/6 background were housed in the standard facility. All animal procedures used in this study were performed in accordance with the protocol approved by the Institutional Animal Care and Use Committee.

Electroconvulsive treatment (ECT) was administered with pulses consisted of 1.0 s, 100 Hz, 18 mA stimulus of 0.3 ms delivered using the Ugo Basile ECT unit (Model 57800) as previously described (A. J. Cole, Neurochem 55, 1920 (1990)). Both Gadd45b WT and KO mice showed similar convulsions. Sham animals were similarly handled in parallel without the current delivery. In some experiments, ±3-(2-carboxypiperazin-4-yl)-propyl-1-phosphonic acid (CPP, 10 mg/kg body weight, i.p.), was injected at 1 hr before ECT. Potential damaging responses after ECT was examined by Western blot and immunostaining of the activated form of caspase (Caspase 3-a; Rabbit; 1:500; Cell Signaling) and phospho-ATM (Ataxia telangiectasia mutated kinase; mouse; Millipore) (3).

Spatial exploration was performed as previously described (V. Ramirez-Amaya et al., *J Neurosci* 25, 1761 (2005)). Briefly, individual adult C57BL/6 mice (Charles River) were placed in the center of a square open box, 60×60 cm with 20-cm-high walls as the novel environment for 1 hr and then immediately processed. Animals in home cages were immediately processed as controls.

For voluntary exercise experiment (running), littermates of adult female KO and WT mice (8 weeks old) were randomly separated into two groups, standard home cage with or without free access to a running wheel that was mounted in the cage as described previously (G. Kronenberg et al., *J Comp Neurol* 467, 455 (2003)). After 7 days, all animals were injected with BrdU (200 mg/kg body weight, i.p.) and sacrificed 2 hrs later for analysis. A separated group of WT animals were sacrificed at different time points after access to running wheels and dentate gyrus tissue was micro-dissected for analysis of Gadd45a and Gadd54b expression.

Quantitative Real-Time Reverse Transcription PCR, In Situ Hybridization and Western Blot Analysis Dentate gyrus tissue was rapidly micro-dissected from adult WT mice, or with ECT, spatial exploration or running. Such dissected tissue was highly enriched for mature neurons with 87±2% (n=4) of all DAPI$^+$ cells that were NeuN$^+$ by immunostaining. For gene expression analysis, total RNA fraction was immediately isolated after dissection (Qiagen), treated with DNAase and reverse-transcribed into the first-strand cDNA (Invitrogen). Specific primers (listed in Table 1) were used in SYBR-green based quantitative real-time PCR to measure the expression level of target genes with the $\Delta\Delta T$ method (ABI). Most primers were designed to span introns to further prevent genomic DNA amplification during the PCR reaction.

For in situ hybridization analysis, 4% paraformamide-fixed cryo-protected brain tissue samples were embedded in O.C.T. mounting solution and frozen at −80° C. Brain sections (20 μm) were cut onto Superfrost-Plus slides (Fisher Scientific). Full-length digoxygenin-labeled antisense riboprobe for Gadd45b was prepared by in vitro transcription. Sections were hybridized with the riboprobes at 65° C. overnight, and washed once in 5×SSC and 1% SDS, then twice in 2×SSC without SDS for 30 min each at 65° C. After overnight incubation with alkaline phosphatase-conjugated anti-digoxygenin antibody at 4° C., hybridized riboprobes were visualized using nitroblue tetrazolium (NBT, 35 μg/ml)/5-bromo-4-chloro-3-indolyl phosphate (BCIP, 18 μg/ml) color reaction at room temperature. For combination of Gadd45b in situ hybridization and immunostaining for Arc, NeuN, DCX or Ki67, Proteinase K treatment was omitted to preserve antigens. After overnight incubation with alkaline phosphatase-conjugated antibody at 4° C., fluorescent signals were obtained using FastRed tablets (Roche). The sections were then subjected to immunostaining for NeuN (mouse; 1:100; Chemicon), DCX (goat; 1:250; Santa Cruz), or Ki67 (rabbit; 1:500; Novocastra). In the case of Arc staining experiments, five digoxygenin-labeled antisense riboprobes of different lengths (100-600 bp) were prepared for Gadd45b and pooled before hybridization to facilitate probe penetration. After the NBT/BCIP color reaction, sections were subjected to immunostaining with antibodies against Arc (rabbit; 1:1000; gift of P. Worley).

For Western blot analysis, freshly dissected dentate gyrus tissues were weighted, homogenized and lysed directly in the SDS sample buffer (62.5 mM Tris pH 6.8, 10% glycerol, 2% SDS, 0.01% bromphenol blue). Protein homogenates were boiled for 10 minutes and loaded into 10-15% SDS PAGE gel for electrophoresis (BioRad). Nitrocellulose membranes with transferred proteins were blocked with 4% BSA in TBS (10 mM Tris-HCl, pH 7.5, 150 mM NaCl), incubated in TBST (TBS+0.05% Tween-20) with primary antibodies, washed and reacted with HRP-conjugated secondary antibodies (Roche) for film development (Pierce). The following primary antibodies were used: rabbit anti-Gadd45b serum (custom made through OpenBiosystem); rabbit anti-BDNF and mouse anti-FGF1 (Santa Cruz); rabbit anti-Arc (gift of P. Worley); mouse anti-ATM-p (Millipore); rabbit anti-Caspase3-a, (Cell Signaling). Membranes were stripped and re-blotted with mouse anti-Actin antibodies (Santa Cruz) for loading control. The relative intensities of the blots were measured by densitometry.

Hippocampal Neuronal Cell Culture, Genetic and Pharmacological Manipulation, Demethylation Reporter Assay, Chromatin Immunoprecipitation Primary hippocampal neurons were prepared from hippocampi of $P_0$ mice and plated on poly-lysine coated coverslips in Neurobasal-A medium supplemented with B27 (Invitrogen) as previously described (H. Song, C. F. Stevens, F. H. Gage, Nature 417, 39 (2002)). AraC (5 µM) was added to eliminate proliferating cells. One-week old culture was used for all experiments. For pharmacological experiments, cultures were pretreated with the following inhibitors 30 minutes before stimulation with $K^+$ (50 mM) or glutamate (20 µM) for 1 hr: BAPTA (50 µM), Nimodipin (10 µM), APV (200 µM), bicuculline (50 µM), KN92 or KN93 (10

A lentiviral vector pFEGW modified from pFUGW (gift of C. Lois) co-expressing shRNA under the U6 promoter and GFP under the EF1α promoter was used (Duan et al., Cell 130, 1146 (2007). The following short hairpin sequences were cloned into the lentiviral vector: AGATTCACTTCAC-CCTGAT (shRNA-Gadd45b#2); TTCTCCGAACGTGT-CACGT (shRNA-Control). Primary hippocampal neuronal cultures were infected with lentiviruses expressing these shRNAs and the efficacy of shRNA on knocking down the expression of endogenous Gadd45b mRNA was analyzed by Q-PCR. Knockdown at the protein level was confirmed in vitro by co-transfection of shRNAs with expression constructs for Gadd45b-GFP in HEK293T cells, followed by Western blot analysis. The efficacy of shRNA knockdown in vivo was further examined by Q-PCR of micro-dissected tissue from animals injected with lentiviruses to co-overexpress GFP and shRNA-Gadd45b#2 or control shRNA for 7 days.

For DNA demethylation reporter assay in cultured primary neurons, a GFP based reporter plasmid (NIT-GFP) was methylated in vitro using bacterial CpG methyltransferase SssI (NEB). Specifically, 5 µg of plasmid DNA was incubated with 10 units of SssI in the recommended buffer containing 800 µM S-adenosylmethionine for 3 hrs at 37° C. Ten units of SssI and 800 µM of S-adenosylmethionine were then added, and the reaction was further incubated for additional 3 hrs. The methylated plasmid was recovered (Qiagen), and complete methylation was confirmed by full protection from HpaII digestion and by bisulfite sequencing. A mammalian expression vector (pCAT) modified from pNIT-GFP with double promoters (CAG promoter to drive tdTomato expression and tTA-inducible CMV promoter to drive cDNA expression) was used to over-express Gadd45b. The open reading frame of Gadd45b was amplified from a cDNA library of mouse dentate gyrus tissue at 1 hr after ECT and cloned into pCAT vector with GFP or FLAG epitope to monitor its expression. Methylated GFP reporter plasmids were mixed (1:3) with expression vector for Gadd45b, shRNA-Gadd45b, or control expressing tdTomato, and co-transfected into primary hippocampal neurons using Lipofectamine-2K at 24 hrs before KCl stimulation. Reporter expression in transfected neurons was monitored at 48 hrs after KCl stimulation by fluorescent microscopy and quantified.

For chromatin immunoprecipitation analysis, E18 primary hippocampal neuronal cultures were used to achieve higher transfection efficacy. Control FLAG or FLAG-Gadd45b expression constructs were electroporated into dissociated neurons before plating (Amaxa) and cultures were subjected to chromatin IP at 7 days in vitro (7 DIV) using antibodies specific to FLAG (Sigma) following manufacture's instruction (Active Motif). Specific primers for FGF-1B, BDNF IX and Oct4 regulatory regions (Table 1) were used in PCR to detect the presence of specific DNA sequences in the FLAG-Gadd45b bound chromatin fraction.

Analysis of Adult Hippocampal Neurogenesis In Vivo

For proliferation assay, adult female Gadd45b WT and KO mice (7-8 weeks) were injected with BrdU (200 mg/kg body weight, i.p.) and sacrificed 2 hrs later. Coronal brain sections (40 µm thick) were prepared and processed for immunostaining using anti-BrdU antibodies (rat; 1:400; Accurate) as previously described (S. Ge et al., Nature 439, 589 (2006)). Images were acquired on a Zeiss LSM 510 Live confocal system (Carl Zeiss). Stereological quantification of $BrdU^+$ cells within the subgranular zone and granule cell layer were carried out as previously described (H. J. Gundersen, E. B. Jensen, J Microsc 147, 229 (1987); M. J. West, L. Slomianka, H. J. Gundersen, Anat Rec 231, 482 (1991); G. Kempermann, H. G. Kuhn, F. H. Gage, Nature 386, 493 (1997)). For Gadd45b knockdown in WT animals, lentiviruses co-expressing shRNA and GFP were concentrated to infect the dentate gyrus with high efficiency as previously described (D. C. Lie et al., Nature 437, 1370 (2005)). Viral stock was stereotaxically injected into the dentate gyrus of adult WT mice at 4 sites (0.5 □l per site at 0.25 □l/min) with the following coordinates (in mm): posterior: 2 from Bregma, lateral: ±1.6, ventral: 2.5; posterior: 3 from Bregma, lateral: ±2.6, ventral: 3.2. Animals were treated with ECT or sham control at 7 days after lentiviral infection. BrdU (200 mg/kg body weight, i.p.) was injected at 10 days after lentiviral infection and sacrificed 2 hrs later. Stereological quantification of $BrdU^+$ cells in the subgranular zone and granule cell layer were carried out only in $GFP^+$ coronal sections. All assessments were performed by observers with no knowledge to animal genotypes or experimental manipulations. Statistical significance (P<0.01) was assessed using the ANOVA test.

For dendritic analysis of newborn neurons, engineered self-inactivating murine retroviruses were used to express GFP specifically in proliferating cells and their progeny (8). High titers of engineered retroviruses ($1 \times 10^9$ unit/ml) were produced by co-transfection of retroviral vectors and VSVG into HEK293gp cells followed by ultra-centrifugation of viral supernatant as previously described (S. Ge et al., Nature 439, 589 (2006). Adult Gadd45b KO and WT mice (7-8 weeks old) housed under standard conditions were used. Retroviruses were stereotaxically injected into the dentate gyrus at 4 sites (0.5 □l per site at 0.25 □l/min) with the following coordinates (in mm): posterior: 2 from Bregma, lateral: ±1.6, ventral: 2.5; posterior: 3 from Bregma, lateral: ±2.6, ventral: 3.2. Mice were sham or ECT treated at 3 days after viral injection and sacrificed at 14 days after viral injection. The dendritic arborisation of newborn neurons was analyzed as previously described (S. Ge et al., Nature 439, 589 (2006). Briefly, three-dimensional (3-D) reconstructions of dendritic processes of each $GFP^+$ neuron were made from Z-series stacks of confocal images. The projection images were semi-automatically traced with NIH ImageJ using the NeuronJ plugin. The total dendritic length of each individual $GFP^+$ neurons was subsequently analyzed. Measurements do not include corrections for inclinations of dendritic processes in Z-plane and therefore represent projected lengths. Assessments were performed by observers with no knowledge to animal genotypes or experimental manipulations. Statistical significance (P<0.01) was assessed using the ANOVA test. The Sholl analysis (13) for dendritic complexity was carried out by counting the number of traced dendrites that cross a series of concentric circles at 5 µm intervals from the cell body. Statistical significance (P<0.05) was assessed using the Student t-test.

Analysis of DNA Methylation in the Adult Dentate Gyrus

MeDIP was carried out similarly as previously described with slight modifications (X. Zhang et al., *Cell* 126, 1189 (2006)). Genomic DNA was isolated from micro-dissected dentate gyrus tissue (QIAGEN). Four µg DNA was digested with MseI overnight into fragments ranging from 200 bp to 1000 bp. Digestion products were purified, denatured and 2 µg DNA was incubated with excess 5-methylcytosine specific antibody (Eurogentec) overnight in 4° C. in IP buffer (20 mM Na-Phosphate pH 7.0, 1M NaCl, 2% Triton-X100) before captured by salmon sperm DNA buffered protein-A agarose beads (Millipore). Beads were extensively washed and incubated in 1× protease digestion buffer (1M Tris-HCl pH 8.0, 0.5M EDTA, 10% SDS) at 55° C. overnight. The DNA was precipitated and purified using phenol chloroform extraction. The enrichment of DNA methylation relative to the input genomic DNA was quantified with Q-PCR using primers for specific regions (listed in Table 1).

For bisulfite sequencing analysis, 1 µg of genomic DNA was bisulfite converted using commercial reagents (Zymo). Sodium bisulfite converts unmethylated cytosines to uracils, but 5-methylcytosines remain unconverted (15). The converted DNA was purified and 50 ng was used as template in the 50 µl PCR reaction using Choice-Taq polymerase (Denville). Specific primers were designed to cover areas of interest with CpG sites (listed in Table 1). Fresh PCR products were purified (Qiagen) and cloned by TOPO-TA cloning method (Invitrogen) and sequenced. Unmethylated cytosines appear as thymines and methylated cytosines appear as cytosines. Efficiency of bisulfite conversion was confirmed by the rare presence of unconverted C residues in non-CpG regions. Statistical significance of methylation levels of each allele was assessed with ANOVA. The exact P value of each comparison is listed in the Table 2.

For methylation-specific PCR analysis, genomic DNA from the dentate gyms tissue of WT mice at different time points after ECTs or after high-titer lentivirus infection without ECT was bisulfite converted, and optimized PCR conditions with primers specific for methylated (M) or un-methylated alleles (UM) of the FGF-1B promoter (listed in Table 1) were used to compare relative methylation levels. PCR products with bisulfite sequencing primers containing no CpG sites were used as input controls.

Culture of Adult Hippocampal Neural Progenitors

Established neural progenitors from adult rat hippocampus were cultured as monolayer as previously described (H. Song, C. F. Stevens, F. H. Gage, *Nature* 417, 39 (2002).). They were maintained on laminin and polyornithine-coated dishes in DMEM/F12 medium containing N2 supplement, L-glutamine (2 mM) and FGF-2 (20 ng/ml). Cultures were passaged for expansion when reaching 70% confluence. For FGF-1 experiments, early-passage, monolayer adherent cultures were plated at the clonal density in the presence of various concentration of FGF-1 or FGF-2 (PeproTech). At 4 days in vitro, cultures were fixed and cell numbers from each condition were determined by counting from randomly selected fields of 4 different biological replicates.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for identifying an agent that modulates DNA demethylation by a Gadd45b polypeptide, the method comprising
   (a) contacting a neuronal cell expressing a Gadd45b polypeptide with an agent; and
   (b) comparing the DNA demethylation activity of the Gadd45b polypeptide in the presence of the agent with the activity in the absence of the agent; wherein a measurable difference in the activity indicates that the agent modulates activity of the polypeptide.

* * * * *

UNITED STATES PATENT AND TRADEMARK OFFICE
CERTIFICATE OF CORRECTION

Page 1 of 1

PATENT NO. : 8,735,071 B2
APPLICATION NO. : 13/142134
DATED : May 27, 2014
INVENTOR(S) : Dengke Ma, Hongjun Song and Guo-li Ming It is certified that error appears in the above-identified patent and that said Letters Patent is hereby corrected as shown below:

In the Specification

On Column 1, Line 19 please replace with this text:
STATEMENT OF GOVERNMENTAL INTEREST
This invention was made with government support under NS047344 and AG024984, awarded by the National Institutes of Health. The government has certain rights in the invention.

Signed and Sealed this
Fourth Day of May, 2021

Drew Hirshfeld
*Performing the Functions and Duties of the*
*Under Secretary of Commerce for Intellectual Property and*
*Director of the United States Patent and Trademark Office*